United States Patent
Wu

(10) Patent No.: US 10,011,592 B2
(45) Date of Patent: Jul. 3, 2018

(54) POLYCYCLIC INHIBITOR OF ANAPLASTIC LYMPHOMA KINASE

(71) Applicant: XUANZHU PHARMA CO., LTD., Shandong (CN)

(72) Inventor: Frank Wu, Shandong (CN)

(73) Assignee: XUANZHU PHARMA CO., LTD., Jinan, Shandong Province (CN)

( * ) Notice: Subject to any disclaimer, the term of this patent is extended or adjusted under 35 U.S.C. 154(b) by 0 days.

(21) Appl. No.: 15/515,056

(22) PCT Filed: Sep. 25, 2015

(86) PCT No.: PCT/CN2015/090712
§ 371 (c)(1),
(2) Date: Mar. 28, 2017

(87) PCT Pub. No.: WO2016/050171
PCT Pub. Date: Apr. 7, 2016

(65) Prior Publication Data
US 2017/0240534 A1 Aug. 24, 2017
US 2018/0086745 A9 Mar. 29, 2018

(30) Foreign Application Priority Data

Sep. 29, 2014 (CN) .......................... 2014 1 0515596

(51) Int. Cl.
*C07D 405/14* (2006.01)
*A61K 31/506* (2006.01)

(52) U.S. Cl.
CPC .......... *C07D 405/14* (2013.01); *A61K 31/506* (2013.01)

(58) Field of Classification Search
CPC .......................... C07D 405/14; C07D 405/00
See application file for complete search history.

(56) References Cited

FOREIGN PATENT DOCUMENTS

| CN | 101921236 A | 12/2010 |
|---|---|---|
| CN | 102459172 A | 5/2012 |
| WO | WO 2004/080980 A1 | 9/2004 |
| WO | WO 2008/073687 A2 | 6/2008 |
| WO | WO 2014/071832 A1 | 5/2014 |
| WO | WO 2014/072419 A1 | 5/2014 |

OTHER PUBLICATIONS

International Search Report for Application No. PCT/CN2015/090712 dated Dec. 25, 2015, 6 pages.
English language abstract for CN 101921236 extracted from espacenet.com database on Apr. 3, 2017, 2 pages.
English language abstract for CN 102459172 extracted from espacenet.com database on Apr. 3, 2017, 2 pages.

*Primary Examiner* — Samira Jean-Louis
(74) *Attorney, Agent, or Firm* — Howard & Howard Attorneys PLLC

(57) ABSTRACT

Disclosed is a polycyclic inhibitor of anaplastic lymphoma kinase as represented by Formula (I), or a pharmaceutically acceptable salt or stereoisomer thereof. Also disclosed is a method for preparing the compound, a pharmaceutical preparation and a pharmaceutical composition comprising the compound, and use of the compound, the pharmaceutically acceptable salt or stereoisomer thereof in manufacture of a medicament for the treatment and/or prevention of, for example, an anaplastic lymphoma kinase-mediated cancer or non-cancer related diseases.

15 Claims, No Drawings

POLYCYCLIC INHIBITOR OF ANAPLASTIC LYMPHOMA KINASE

CROSS-REFERENCE TO RELATED APPLICATIONS

This application is the National Stage of International Patent Application No. PCT/CN2015/090712, filed on Sep. 25, 2015, which claims priority to and all the advantages of Chinese Patent Application No. 201410515596.9, filed on Sep. 29, 2014, the contents of which are incorporated herein by reference.

TECHNICAL FIELD

The invention relates to a polycyclic inhibitor of anaplastic lymphoma kinase, or a pharmaceutically acceptable salt or a stereoisomer thereof, a method for preparing the compound, a pharmaceutical preparation and a pharmaceutical composition comprising the compound, and use of the compound, or a pharmaceutically acceptable salt or stereoisomer thereof in manufacture of a medicament for the treatment and/or prevention of an anaplastic lymphoma kinase-mediated cancer or non-cancer related diseases.

BACKGROUND ART

Anaplastic lymphoma kinase (ALK) is a member of receptor tyrosine kinase family, which can recruit downstream protein by autophosphorylation, and further modulate cell metabolism and growth by expression of a specific gene. Anaplastic lymphoma kinase was first found in Anaplastic large cell lymphoma (ALCL), and was also found later to be expressed in a high level in non-small cell lung cancer (NSCLC).

The abnormal expression of ALK in some ALCL/NSCLC was resulted from different chromosomal translocations. These chromosomal translocations may result in the production of the corresponding fusion proteins. The analysis of these fusion genes shows that they all comprise a 3' terminal gene sequence of ALK gene, which encodes an intracellular kinase domain; and the gene fragments fused to ALK all comprise a promoter element and encode a sequence that mediates self-dimerization, thus resulting in high expression and over-activation of the fusion protein having ALK kinase activity, and causing malignant transformation of cell. Therefore, the activity of intracellular kinase domain of ALK and the corresponding signal transduction pathway are the important molecular mechanism responsible for the development of ALCL. In addition to ALK, ROS1 is another hot target gene studied in lung adenocarcinoma. ROS1 is a member of receptor tyrosine kinase family. ROS1 is responsible for an incidence rate of about 1.7% for NSCLC. ROS1 and Anaplastic lymphoma kinase (ALK) have a homology of 49% in kinase domain, and have an identity of 77% in ATP-binding site, which makes the treatment of NSCLC with ROS1 rearrangement by using ALK kinase inhibitor possible.

Therefore, the development of small molecular inhibitors against ALK/ROS1 may effectively reduce the effect of the mutated ALK/ROS1 gene on downstream proteins, thereby influencing invasion and proliferation of tumor cells, and the like, and finally influencing the growth of tumor cells and exerting anti-tumor effect. Crizotinib developed by Pfizer has come into the market successfully now, and has been widely accepted as it has good therapeutic effect against EML4-ALK mutated non-small cell lung cancer. With the appearance of Crizotinib on the market, specific diagnostic kits have also come into market. Before the application of a medicament, a patient is diagnosed by a kit to determine whether he or she has ALK mutation. For specific patients, ALK inhibitors exhibit good inhibitory activity. The research on Crizotinib against ROS1 has been in the clinic stage, and achieved a breakthrough role in pharmacotherapy. However, there are a lot of clinical trials showing that patients having ALK fusion generally exhibit resistance to Crizotinib after 1-2 years treatment. The mechanism underlying the generation of resistance to Crizotinib is very complex, wherein ALK mutation is responsible for about ⅓ of resistance cases, and the mutation sites mainly include L1196M, C1156Y, F1174L, etc. Therefore, it is of great clinical significance to design and screen the second generation ALK inhibitors having good therapeutic effect in patients resistant to Crizotinib.

The second generation ALK inhibitors, which have come into the market now, include Ceritinib from Novartis, and Alectinib from Chugai Pharmaceutical Co. Ltd. under Roche; and the ALK inhibitors in clinical stage include AZD-3463, AP26113, etc.

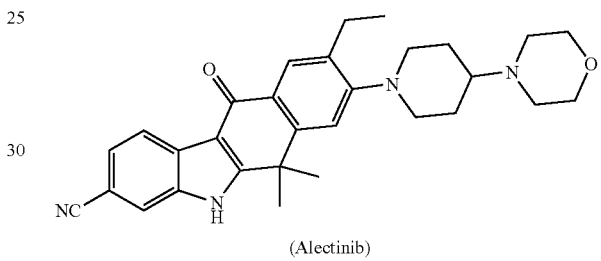

(Alectinib)

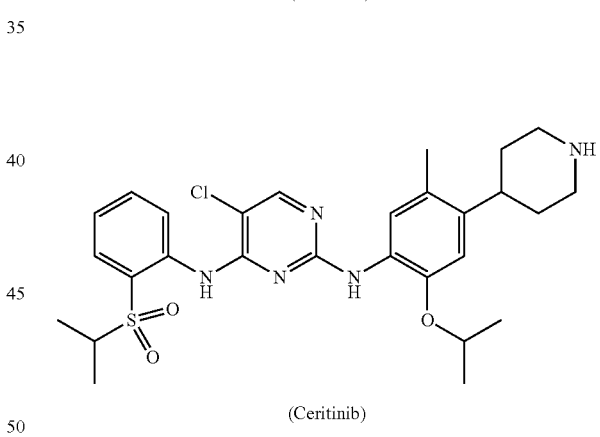

(Ceritinib)

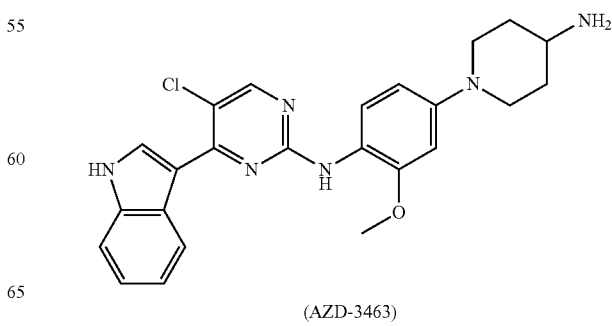

(AZD-3463)

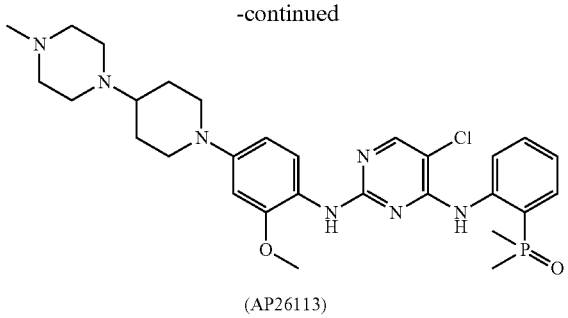

(AP26113)

Therefore, it is of great significance for the treatment of diseases caused by ALK mutation in clinic to look for new small molecular compounds having excellent inhibitory activity against ALK fusion and drug resistant mutations by modifying a compound structure, make great efforts to improve physico-chemical properties of compounds, and enhance druggability, such as bioavailability of compounds.

Contents of Invention

In order to develop small molecular inhibitors against ALK, Examples of the invention provide a polycyclic inhibitor of anaplastic lymphoma kinase having good effect on the treatment and/or prevention of an ALK-mediated cancer or non-cancer related disease. The technical solutions are as follows:

Solution 1. A Compound of Formula (I), or a Pharmaceutically Acceptable Salt or Stereoisomer Thereof:

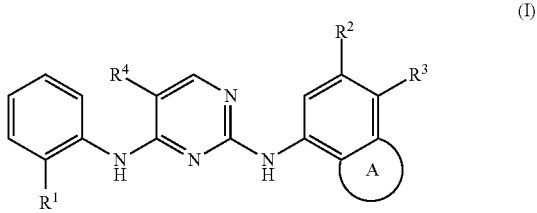

wherein, $R^1$ is selected from the group consisting of —$COR^5$, —$CO_2R^5$, —$CONRR^5$, —$SOR^5$, —$SO_2R^5$ and —$SO_2NRR^5$;

$R^2$ is selected from the group consisting of hydrogen atom, halogen atom, nitro, cyano, amino, hydroxyl, carboxyl, $C_{1-6}$alkyl, hydroxy$C_{1-6}$alkyl, halo-$C_{1-6}$alkyl, amino$C_{1-6}$alkyl, $C_{1-6}$alkoxy, hydroxy$C_{1-6}$alkoxy, halo-$C_{1-6}$alkoxy, $C_{2-8}$alkenyl, $C_{2-8}$alkynyl, $C_{1-6}$alkylthio, $C_{1-6}$alkylcarbonyl, $C_{1-6}$alkylcarbonyloxy, $C_{1-6}$alkylsulfonamido, $C_{1-6}$alkylaminosulfonyl, ($C_{1-6}$alkyl)$_2$aminosulfonyl and $C_{1-6}$alkylsulfonyl;

$R^3$ is selected from the group consisting of 5-14 membered heteroaryl optionally substituted with 1-3 substituent(s) W, and 3-8 membered heterocyclyl optionally substituted with 1-3 substituent(s) W, W is selected from the group consisting of hydroxyl, amino, carboxyl, cyano, nitro, halogen atom, $C_{1-6}$alkyl, $C_{1-6}$alkoxy, $C_{1-6}$alkylamino, ($C_{1-6}$alkyl)$_2$amino, halo-$C_{1-6}$alkyl, halo-$C_{1-6}$alkoxy, $C_{1-6}$alkoxy$C_{1-6}$alkyl, $C_{1-6}$alkylcarbonyl, $C_{1-6}$alkylcarbonyloxy, $C_{1-6}$alkylsulfonyl, $C_{2-8}$alkenyl and $C_{2-8}$alkynyl;

$R^4$ is selected from the group consisting of hydrogen atom, halogen atom, cyano, nitro, amino, hydroxyl, carboxyl, $C_{1-6}$alkoxy, 3-8 membered carbon ring-O—, $C_{1-6}$alkyl, hydroxy$C_{1-6}$alkyl, halo-$C_{1-6}$alkyl, hydroxy$C_{1-6}$alkoxy, halo-$C_{1-6}$alkoxy, $C_{2-8}$alkenyl, $C_{2-8}$alkynyl, $C_{1-6}$alkylamino, $C_{1-6}$alkylcarbonyl, $C_{1-6}$alkylcarbonyloxy and ($C_{1-6}$alkyl)$_2$amino;

R and $R^5$ are independently selected from the group consisting of hydrogen atom, $C_{1-6}$alkyl and 3-8 membered carbon ring;

A is selected from the group consisting of 3-8 membered cycloalkyl optionally substituted with substituent Q, 4-5 membered heterocyclyl containing two O, S and/or N atoms that is optionally substituted with substituent Q, and 6-8 membered heterocyclyl containing 1-2 O, S and/or N atom(s) that is optionally substituted with substituent Q; the substituent Q is selected from the group consisting of hydroxyl, amino, carboxyl, cyano, nitro, halogen atom, $C_{1-6}$alkyl, $C_{1-6}$alkoxy, $C_{1-6}$alkylamino, ($C_{1-6}$alkyl)$_2$amino, halo-$C_{1-6}$alkyl, halo-$C_{1-6}$alkoxy, $C_{1-6}$alkoxy$C_{1-6}$alkyl, $C_{2-8}$alkenyl, $C_{2-8}$alkynyl and 3-8 membered heterocyclyl.

Solution 2. The Compound, or the Pharmaceutically Acceptable Salt or Stereoisomer Thereof According to Solution 1, wherein, $R^1$ is selected from the group consisting of —$CO_2R^5$, —$CONRR^5$, —$SO_2R^5$ and —$SO_2NRR^5$;

$R^2$ is selected from the group consisting of hydrogen atom, halogen atom, nitro, cyano, amino, hydroxyl, carboxyl, $C_{1-6}$alkyl, hydroxy$C_{1-6}$alkyl and halo-$C_{1-6}$alkyl;

$R^3$ is selected from the group consisting of 5-8 membered heteroaryl containing 1-2 O, S and/or N atom(s) that is optionally substituted with 1-2 substituent(s) W, and 4-6 membered heterocyclyl containing 1-2 O, S and/or N atom(s) that is optionally substituted with 1-2 substituent(s) W, W is selected from the group consisting of hydroxyl, amino, carboxyl, cyano, nitro, halogen atom, $C_{1-6}$alkyl, $C_{1-6}$alkoxy, $C_{1-6}$alkylamino, ($C_{1-6}$alkyl)$_2$amino, halo-$C_{1-6}$alkyl, halo-$C_{1-6}$alkoxy, $C_{1-6}$alkoxy$C_{1-6}$alkyl, $C_{1-6}$alkylcarbonyl, $C_{1-6}$alkylcarbonyloxy, $C_{1-6}$alkylsulfonyl, $C_{2-8}$alkenyl and $C_{2-8}$alkynyl;

$R^4$ is selected from the group consisting of hydrogen atom, halogen atom, cyano, nitro, amino, hydroxyl, carboxyl, $C_{1-6}$alkoxy, $C_{1-6}$alkyl, hydroxy$C_{1-6}$alkyl, halo-$C_{1-6}$alkyl, hydroxy$C_{1-6}$alkoxy, halo-$C_{1-6}$alkoxy, $C_{1-6}$alkylamino, $C_{1-6}$alkylcarbonyl and $C_{1-6}$alkylcarbonyloxy;

R and $R^5$ are independently selected from the group consisting of hydrogen atom, $C_{1-6}$alkyl and 5-6 membered saturated or partially saturated carbon ring;

A is selected from the group consisting of 5-6 membered cycloalkyl optionally substituted with substituent Q, 4-5 membered heterocyclyl containing two O, S and/or N atoms that is optionally substituted with substituent Q, and 6-7 membered heterocyclyl containing 1-2 O, S and/or N atom(s) that is optionally substituted with substituent Q; the substituent Q is selected from the group consisting of hydroxyl, amino, carboxyl, cyano, nitro, halogen atom and $C_{1-6}$alkyl.

Solution 3. The Compound, or the Pharmaceutically Acceptable Salt or Stereoisomer Thereof According to Solution 2, wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl and $C_{1-6}$alkyl;

$R^3$ is selected from the group consisting of 5-6 membered heteroaryl containing 1-2 N atom(s) that is optionally substituted with 1-2 substituent(s) W, and 4-6 membered heterocyclyl containing 1-2 N atom(s) that is optionally substituted with 1-2 substituent(s) W, W is selected from the group consisting of hydroxyl, amino, carboxyl, cyano, nitro, halogen atom, $C_{1-6}$alkyl, $C_{1-6}$alkoxy, $C_{1-6}$alkylamino, $(C_{1-6}$alkyl$)_2$amino, halo-$C_{1-6}$alkyl, halo-$C_{1-6}$alkoxy, $C_{1-6}$alkylcarbonyl, $C_{1-6}$alkylcarbonyloxy and $C_{1-6}$alkylsulfonyl;

$R^4$ is selected from the group consisting of hydrogen atom, halogen atom, cyano, nitro, amino, hydroxyl, carboxyl, $C_{1-6}$alkoxy, $C_{1-6}$alkyl, halo-$C_{1-6}$alkyl, $C_{1-6}$alkylamino, $C_{1-6}$alkylcarbonyl and $C_{1-6}$alkylcarbonyloxy;

R and $R^5$ are independently selected from the group consisting of hydrogen atom and $C_{1-6}$alkyl;

A is selected from the group consisting of 5 membered heterocyclyl containing two O, S and/or N atoms that is optionally substituted with 1-2 substituent(s) Q, and 6 membered heterocyclyl containing 1-2 O, S and/or N atom(s) that is optionally substituted with 1-2 substituent(s) Q; the substituent Q is selected from the group consisting of hydroxyl, amino, carboxyl, cyano, nitro, halogen atom and $C_{1-6}$alkyl.

Solution 4. The Compound, or the Pharmaceutically Acceptable Salt or Stereoisomer Thereof According to Solution 3, wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl and $C_{1-6}$alkyl;

$R^3$ is selected from 4-6 membered heterocyclyl containing 1-2 N atom(s) that is optionally substituted with 1-2 substituent(s) W;

W is selected from the group consisting of hydroxyl, amino, carboxyl, cyano, nitro, halogen atom, $C_{1-4}$alkyl, $C_{1-4}$alkoxy, $C_{1-4}$alkylamino, $(C_{1-4}$alkyl$)_2$amino, halo-$C_{1-4}$alkyl, halo-$C_{1-4}$alkoxy, $C_{1-4}$alkylcarbonyl, $C_{1-4}$alkylcarbonyloxy and $C_{1-4}$alkylsulfonyl;

$R^4$ is selected from the group consisting of fluorine atom, bromine atom and chlorine atom;

R and $R^5$ are independently selected from $C_{1-4}$alkyl;

A is selected from the group consisting of 5 membered heterocyclyl containing two O, S and/or N atoms and 6 membered heterocyclyl containing 1-2 O, S and/or N atom(s), optionally substituted with one substituent Q; the substituent Q is selected from the group consisting of hydroxyl, amino, carboxyl, cyano, nitro, halogen atom and $C_{1-4}$alkyl.

Solution 5. The Compound, or the Pharmaceutically Acceptable Salt or Stereoisomer Thereof According to Solution 3, wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl and $C_{1-4}$alkyl;

$R^3$ is selected from the group consisting of pyridinyl, dihydropyridinyl, tetrahydropyridinyl, azetidinyl, pyrrolyl, dihydropyrrolyl, tetrahydropyrrolyl, pyrazolyl, dihydropyrazolyl, tetrahydropyrazolyl, imidazolyl, dihydroimidazolyl, tetrahydroimidazolyl, pyrimidinyl, dihydropyrimidinyl, tetrahydropyrimidinyl, piperidyl, piperazinyl and morpholinyl;

$R^4$ is selected from the group consisting of fluorine atom, bromine atom and chlorine atom;

R and $R^5$ are independently selected from $C_{1-4}$alkyl;

A is selected from the group consisting of 5 membered heterocyclyl containing two oxygen atoms and 6 membered heterocyclyl containing 1-2 oxygen atom(s), optionally substituted with one substituent Q; the substituent Q is selected from the group consisting of hydroxyl, amino, carboxyl, cyano, nitro, halogen atom and $C_{1-4}$alkyl.

Solution 6. The Compound, or the Pharmaceutically Acceptable Salt or Stereoisomer Thereof According to Solution 5, wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl, methyl, ethyl, propyl, isopropyl, butyl, isobutyl and tert-butyl;

$R^3$ is selected from the group consisting of pyridinyl, dihydropyridinyl, tetrahydropyridinyl, pyrrolyl, dihydropyrrolyl, tetrahydropyrrolyl, azetidinyl, piperidyl, piperazinyl and morpholinyl;

$R^4$ is selected from the group consisting of fluorine atom, bromine atom and chlorine atom;

R and $R^5$ are independently selected from the group consisting of methyl, ethyl, propyl, isopropyl, butyl, isobutyl and tert-butyl;

A is selected from 6 membered heterocyclyl containing two oxygen atoms that is optionally substituted with one substituent Q; the substituent Q is selected from the group consisting of hydroxyl, amino, carboxyl, cyano, nitro, halogen atom, methyl, ethyl, propyl, isopropyl, butyl, isobutyl and tert-butyl.

Solution 7. The Compound, or the Pharmaceutically Acceptable Salt or Stereoisomer Thereof According to Solution 5, wherein, $R^3$ is selected from the group consisting of tetrahydropyridinyl, azetidinyl, tetrahydropyrrolyl, tetrahydropyrazolyl, tetrahydroimidazolyl, tetrahydropyrimidinyl, piperidyl, piperazinyl and morpholinyl;

A is selected from 5 membered heterocyclyl containing two oxygen atoms that is optionally substituted with one substituent Q; the substituent Q is selected from the group consisting of hydroxyl, amino, carboxyl, cyano, nitro, halogen atom and $C_{1-4}$alkyl.

Solution 8. The Compound, or the Pharmaceutically Acceptable Salt or Stereoisomer Thereof According to Solution 5, wherein, $R^3$ is selected from the group consisting of tetrahydropyridinyl, azetidinyl, tetrahydropyrrolyl, pyrazolyl, tetrahydroimidazolyl, tetrahydropyrimidinyl, piperidyl, piperazinyl and morpholinyl;

A is selected from 6 membered heterocyclyl containing two oxygen atoms that is optionally substituted with one substituent Q; the substituent Q is selected from the group consisting of hydroxyl, amino, carboxyl, cyano, nitro, halogen atom and $C_{1-4}$alkyl.

Solution 9. The Compound, or the Pharmaceutically Acceptable Salt or Stereoisomer Thereof According to Solution 5, wherein, $R^3$ is selected from the group consisting of pyridinyl, dihydropyridinyl, tetrahydropyridinyl, pyrrolyl, dihydropyrrolyl, tetrahydropyrrolyl, azetidinyl, piperidyl, piperazinyl and morpholinyl;

A is selected from 6 membered heterocyclyl containing one oxygen atom, optionally substituted with one substituent Q; the substituent Q is selected from the group consisting of hydroxyl, amino, carboxyl, cyano, nitro, halogen atom and $C_{1-4}$alkyl.

Solution 10. The Compound, or the Pharmaceutically Acceptable Salt or Stereoisomer Thereof According to Solution 3, wherein, $R^3$ is selected from 4-6 membered partially saturated heterocyclyl containing 1-2 nitrogen atom(s) that is optionally substituted with 1-2 substituent(s) W, and $R^3$ is linked to phenyl via carbon atom;

W is selected from the group consisting of hydroxyl, amino, carboxyl, cyano, nitro, halogen atom, $C_{1-6}$alkyl, $C_{1-6}$alkoxy, $C_{1-6}$alkylamino, $(C_{1-6}$alkyl$)_2$amino, halo-$C_{1-6}$alkyl, halo-$C_{1-6}$alkoxy, $C_{1-6}$alkylcarbonyl, $C_{1-6}$alkylcarbonyloxy and $C_{1-6}$alkylsulfonyl;

A is selected from 6 membered heterocyclyl containing one O, S and/or N atom, optionally substituted with 1-2 substituent(s) Q; the substituent Q is selected from the group consisting of hydroxyl, amino, carboxyl, cyano, nitro, halogen atom and $C_{1-6}$alkyl.

Solution 11. The Compound, or the Pharmaceutically Acceptable Salt or Stereoisomer Thereof According to Solution 3, wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl and $C_{1-6}$alkyl;

$R^3$ is selected from 4-6 membered saturated heterocyclyl containing 1-2 N atom(s) that is optionally substituted with 1-2 substituent(s) W, and $R^3$ is linked to phenyl via carbon atom;

W is selected from the group consisting of hydroxyl, amino, carboxyl, cyano, nitro, halogen atom, $C_{1-6}$alkyl, $C_{1-6}$alkoxy and $C_{1-6}$alkylamino;

$R^4$ is selected from the group consisting of hydrogen atom, halogen atom, cyano, nitro, amino, hydroxyl, carboxyl, $C_{1-6}$alkoxy and $C_{1-6}$alkyl;

R and $R^5$ are independently selected from the group consisting of hydrogen atom and $C_{1-6}$alkyl;

A is selected from the group consisting of 5 membered heterocyclyl containing two oxygen atoms that is optionally substituted with 1-2 substituent(s) Q, and 6 membered heterocyclyl containing 1-2 oxygen atom(s) that is optionally substituted with 1-2 substituent(s) Q; the substituent Q is selected from the group consisting of hydroxyl, amino, carboxyl, cyano, nitro, halogen atom and $C_{1-6}$alkyl.

Solution 12. The Compound, or the Pharmaceutically Acceptable Salt or Stereoisomer Thereof According to Solution 3, wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl and $C_{1-4}$alkyl;

$R^3$ is selected from the group consisting of pyridinyl, dihydropyridinyl, tetrahydropyridinyl, azetidinyl, pyrrolyl, dihydropyrrolyl, tetrahydropyrrolyl, piperidyl, piperazinyl and morpholinyl;

$R^4$ is selected from the group consisting of fluorine atom, bromine atom and chlorine atom;

R and $R^5$ are independently selected from $C_{1-4}$alkyl;

A is selected from 5 membered heterocyclyl containing two N atoms and 6 membered heterocyclyl containing 1-2 N atom(s), optionally substituted with 1-2 substituent(s) Q; the substituent Q is selected from the group consisting of hydroxyl, amino, carboxyl, cyano, nitro, halogen atom and $C_{1-4}$alkyl.

A Part of Compounds of the Invention

| No. | Structural formula |
|---|---|
| 1 | |
| 2 | |
| 3 | |
| 4 | |
| 5 | |

| No. | Structural formula |
|---|---|
| 6 | |
| 7 | |
| 8 | |
| 9 | |
| 10 | |

SPECIFIC MODES FOR CARRYING OUT THE INVENTION

In order to make the purpose of Examples, the technical solutions and advantages of the invention clearer, the technical solutions of Examples of the invention are described clearly and completely as follows. Obviously, the examples described are a part of examples of the invention, rather than all the examples. Based on the examples of the invention described, all the other examples, as obtained by a person skilled in the art without paying creative work, also fall into the protection scope of the invention.

The term "halogen" used herein refers to fluorine, chlorine, bromine, and iodine atom, etc.

The term "$C_{1-6}$alkyl" used herein refers to linear or branched alkyl containing 1-6 carbon atoms, including, e.g., "$C_{1-4}$alkyl", "$C_{1-3}$alkyl" and the like. Its examples include, but are not limited to methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-metylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc.

The term "$C_{2-8}$alkenyl" used herein refers to linear, branched or cyclic alkenyl containing 2-8 carbon atoms and at least one double bond, including, e.g., "$C_{2-6}$alkenyl", "$C_{2-4}$alkenyl", "$C_{2-3}$alkenyl", "$C_{3-6}$cycloalkenyl" and the like. Its examples include, but are not limited to vinyl, 1-propenyl, 2-propenyl, 2-butenyl, 3-butenyl, 2-methyl-1-propenyl, 1-methyl-2-propenyl, 1-pentenyl, 2-pentenyl, 3-pentenyl, 2-methyl-1-butenyl, 3-methyl-1-butenyl, 2-methyl-3-butenyl, 1,1-dimethyl-2-propenyl, 1-ethyl-2-propenyl, 2-hexenyl, 3-hexenyl, 2-methyl-1-pentenyl, 3-methyl-1-pentenyl, 1-methyl-2-pentenyl, 3-methyl-2-pentenyl, 2-methyl-3-pentenyl, 1-methyl-4-pentenyl, 3-methyl-4-pentenyl, 1,1-dimethyl-3-butenyl, 1,2-dimethyl-3-butenyl, 1,3-dimethyl-2-butenyl, 2,2-dimethyl-3-butenyl, 2,3-dimethyl-2-butenyl, 2,3-dimethyl-1-butenyl, 2-ethyl-1-butenyl, 2-ethyl-3-butenyl, 2-heptenyl, 3-heptenyl, 4-heptenyl, 1-octenyl, 3-octenyl, 4-octenyl, 1,3-butadienyl, 2,4-pentadienyl, 1,4-hexadienyl, 2,4-hexadienyl, 1,5-heptadienyl, 2,5-heptadienyl, 2,6-octadienyl, cyclopentenyl, 1,3-cyclopentadienyl, cyclohexenyl, 1,4-cyclohexadienyl, cycloheptenyl, 1,4-cycloheptadienyl, cyclooctenyl, etc.

The term "$C_{2-8}$alkynyl" used herein refers to linear or branched alkynyl of 2-8 carbon atoms containing triple bond, including, e.g., "$C_{2-6}$alkynyl", "$C_{2-4}$alkynyl", "$C_{2-3}$alkynyl" and the like. Its examples include, but are not limited to acetenyl, 1-propynyl, 2-butynyl, 1-methyl-2-propynyl, 2-pentynyl, 3-pentynyl, 1-methyl-2-butynyl, 2-methyl-3-butynyl, 1,1-dimethyl-2-propynyl, 1-ethyl-2-propynyl, 2-hexynyl, 3-hexynyl, 1-methyl-2-pentynyl, 1-methyl-3-pentynyl, 2-methyl-3-pentynyl, 1,1-dimethyl-3-butynyl, 2-ethyl-3-butynyl, 2-heptynyl, 3-heptynyl, 4-methyl-2-hexynyl, 5-methyl-2-hexynyl, 2-methyl-3-hexynyl, 5-methyl-3-hexynyl, 2-methyl-4-hexynyl, 4-methyl-5-hexynyl, 2-octynyl, 3-octynyl, 4-octynyl, 4-methyl-2-heptynyl, 5-methyl-3-heptynyl, 6-methyl-3-heptynyl, 2-methyl-4-heptynyl, 2-methyl-5-heptynyl, 3-methyl-6-heptynyl, etc.

The terms "$C_{1-6}$alkoxy, $C_{1-6}$alkylamino, $(C_{1-6}$alkyl$)_2$amino, $C_{1-6}$alkylthio, $C_{1-6}$alkylcarbonyl, $C_{1-6}$alkylsulfonamido, $C_{1-6}$alkylaminosulfonyl, $(C_{1-6}$alkyl$)_2$aminosulfonyl, $C_{1-6}$alkylsulfonyl, $C_{1-6}$alkylcarbonyloxy" used herein refer to the groups in the form of $C_{1-6}$alkyl-O—, $C_{1-6}$alkyl-NH—, $(C_{1-6}$alkyl$)_2$-N—, $C_{1-6}$alkyl-S—, $C_{1-6}$alkyl-C(O)—, $C_{1-6}$alkyl-SO$_2$NH—, $C_{1-6}$alkyl-NHSO$_2$—, $(C_{1-6}$alkyl$)_2$-NSO$_2$—, $C_{1-6}$alkyl-SO$_2$—, $C_{1-6}$alkyl-C(O)—O—, wherein "$C_{1-6}$alkyl" has the same meanings as defined above.

The terms "$C_{1-4}$alkoxy, $C_{1-4}$alkylamino, $(C_{1-4}$alkyl$)_2$amino, $C_{1-4}$alkylthio, $C_{1-4}$alkylcarbonyl, $C_{1-4}$alkylsulfonamido, $C_{1-4}$alkylaminosulfonyl, $(C_{1-4}$alkyl$)_2$aminosulfonyl, $C_{1-4}$alkylsulfonyl, $C_{1-4}$alkylcarbonyloxy" used herein refer to the groups in the form of $C_{1-4}$alkyl-O—, $C_{1-4}$alkyl-NH—, $(C_{1-4}$alkyl$)_2$-N—, $C_{1-4}$alkyl-S—, $C_{1-4}$alkyl-C(O)—, $C_{1-4}$alkyl-$SO_2$NH—, $C_{1-4}$alkyl-NHSO$_2$—, ($C_{1-4}$alkyl)$_2$-NSO$_2$—, $C_{1-4}$alkyl-$SO_2$—, $C_{1-4}$alkyl-C(O)—O—, wherein the term "$C_{1-4}$alkyl" has the same meanings as defined above.

The terms "halo-$C_{1-6}$alkyl, hydroxy$C_{1-6}$alkyl, amino$C_{1-6}$ alkyl, $C_{1-6}$alkoxy$C_{1-6}$alkyl, hydroxy$C_{1-8}$alkenyl, carboxy$C_{1-8}$ alkenyl, hydroxy$C_{1-8}$alkynyl, carboxy$C_{1-8}$alkynyl, halo-$C_{1-6}$alkoxy, hydroxy$C_{1-6}$alkoxy, $C_{1-6}$alkoxy$C_{1-6}$alkoxy, hydroxy$C_{1-6}$alkylamino" used herein refer to the groups formed by substituting the hydrogen atom(s) of $C_{1-6}$alkyl, $C_{1-8}$alkenyl, $C_{1-8}$alkynyl, $C_{1-6}$alkoxy, $C_{1-6}$alkylamino with one or more, e.g., 1-4, 1-3, 1-2 halogen atom(s), hydroxyl, amino, carboxyl, $C_{1-6}$alkoxy, respectively.

The terms "halo-$C_{1-4}$alkyl, hydroxy$C_{1-4}$alkyl, amino$C_{1-4}$ alkyl, $C_{1-4}$alkoxy$C_{1-4}$alkyl, hydroxy$C_{2-6}$alkenyl, carboxy$C_{2-6}$ alkenyl, hydroxy$C_{2-6}$alkynyl, carboxy$C_{2-6}$alkynyl, halo-$C_{1-4}$alkoxy, hydroxy$C_{1-4}$alkoxy, $C_{1-4}$alkoxy$C_{1-4}$alkoxy, hydroxy$C_{1-4}$alkylamino" used herein refer to the groups formed by substituting the hydrogen atom(s) of $C_{1-4}$alkyl, $C_{2-6}$alkenyl, $C_{2-6}$alkynyl, $C_{1-4}$alkoxy, $C_{1-4}$alkylamino with one or more, e.g., 1-4, 1-3, 1-2 halogen atom(s), hydroxyl, amino, carboxyl, $C_{1-4}$alkoxy, respectively.

The term "3-8 membered cycloalkyl" used herein refers to a monocyclic alkyl derived from removal of one hydrogen from a $C_{3-8}$alkyl moiety, including, e.g., "3-6 membered cycloalkyl", "4-7 membered cycloalkyl", "4-6 membered cycloalkyl", "5-6 membered cycloalkyl", etc. Its examples include, but are not limited to: cyclopropyl, cyclobutyl, cyclopentyl, cyclohexyl, cycloheptyl, cyclooctyl, methylcyclopropyl, dimethylcyclopropyl, methylcyclobutyl, dimethylcyclobutyl, methylcyclopentyl, dimethylcyclopentyl, methylcyclohexyl, dimethylcyclohexyl, etc.

The term "5-14 membered heteroaryl" used herein refers to heteroaryl of 5-14 cycloatoms containing at least one heteroatom, including "5-8 membered heteroaryl", "6-14 membered fused heteroaryl", wherein the heteroatom is N, O or S, etc., and it also includes the circumstance where carbon atom, nitrogen atom or sulfur atom is oxo. For example, it may be "5-8 membered heteroaryl containing 1-3 O, S and/or N atom(s)", "5-8 membered heteroaryl containing 1-2 O, S and/or N atom(s)", "5-8 membered heteroaryl containing 2-3 O, S and/or N atoms".

The term "5-8 membered heteroaryl" used herein, includes, e.g., "5-7 membered heteroaryl", "5-6 membered heteroaryl", and the like. For example, it may be "5-6 membered heteroaryl containing 1-2 nitrogen atom(s)", "5-6 membered heteroaryl containing 2-3 N atoms". Its examples include, but are not limited to furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridinyl, 2-pyridinone, 4-pyridinone, pyrimidinyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azacycloheptatrienyl, 1,3-diazacycloheptatrienyl, azacyclooctatetraenyl, etc., preferably "5-6 membered heteroaryl".

The term "6-14 membered fused heteroaryl" used herein, includes, e.g., "6-10 membered fused heteroaryl", "7-10 membered fused heteroaryl", "9-10 membered fused heteroaryl", etc. Its examples include, but are not limited to: benzofuranyl, isobenzofuranyl, benzothienyl, indolyl, isoindolyl, benzoxazolyl, benzoimidazolyl, indazolyl, benzotriazolyl, quinolinyl, quinolin-2-one, quinolin-4-one, isoquinolin-1-one, isoquinolinyl, aziridinyl, phenanthridinyl, benzopyridazinyl, phthalazinyl, quinazolinyl, quinoxalinyl, phenazinyl, pteridinyl, purinyl, naphthyridinyl, phenthiazine, etc.

The term "3-8 membered heterocyclyl" used herein refers to a group derived from removal of a hydrogen from a saturated or partially saturated monocyclic heterocyclic compound containing 3-8 cycloatoms and at least one heteroatom (e.g., 1, 2, 3, 4 or 5 heteroatoms). For example, it includes "3-7 membered heterocyclyl", "3-6 membered heterocyclyl", "3-5 membered heterocyclyl", "4-7 membered heterocyclyl", "4-6 membered heterocyclyl", "4-5 membered heterocyclyl", "5-6 membered heterocyclyl", "5-7 membered heterocyclyl", "5-8 membered heterocyclyl", "6-7 membered heterocyclyl", "6-8 membered heterocyclyl", etc. For example, it may be "3-5 membered heterocyclyl containing two O, S and/or N atoms", "6-8 membered heterocyclyl containing 1-2 O, S and/or N atom(s)", "4-6 membered heterocyclyl containing 1-2 O, S and/or N atom(s)", "4-5 membered heterocyclyl containing two O, S and/or N atoms", "6-7 membered heterocyclyl containing 1-2 O, S and/or N atom(s)", "5 membered heterocyclyl containing two O, S and/or N atoms", "6 membered heterocyclyl containing 1-2 O, S and/or N atom(s)", "5 membered heterocyclyl containing two N atoms", "6 membered heterocyclyl containing 1-2 N atom(s)", "5 membered heterocyclyl containing two oxygen atoms", "6 membered heterocyclyl containing 1-2 oxygen atom(s)", "6 membered heterocyclyl containing two oxygen atoms", "5-6 membered heterocyclyl containing two oxygen atoms", "6 membered heterocyclyl containing one O, S and/or N atom", "4-6 membered heterocyclyl containing 1-2 N atom(s)". 3-8 membered partially saturated mono-heterocyclyl refers to a cyclic group containing double bond and heteroatom. 3-8 membered saturated mono-heterocyclyl refers to a heteroatom-containing cyclic group having all the bonds saturated. Its examples include, but are not limited to: aziridinyl, 2H-aziridinyl, diaza cyclopropyl, 3H-diazacyclopropenyl, azetidinyl, 1,4-dioxacyclohexyl, 1,3-dioxacyclohexyl, 1,3-dioxacyclopentyl, 1,4-dioxacyclohexadienyl, tetrahydrofuryl, dihydropyridinyl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, dihydropyrimidinyl, tetrahydropyrimidinyl, piperidyl, piperazinyl, morpholinyl, 4,5-dihydrooxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 2H-pyran-2-one-yl, 3,4-dihydro-2H-pyranyl, 2,5-dihydrothienyl, 3,4-dihydro-2H-pyranyl, 5,6-dihydro-4H-1,3-oxazinyl, 1,2,3,6-tetrahydropyridinyl, 1,2,3,4-tetrahydropyridinyl, 2,3,4,5-tetrahydropyridinyl, etc., preferably "5-6 membered heterocyclyl".

The term "heteroatom" used herein refers to N, O, C(O), S, SO and/or $SO_2$, etc., preferably, N, O, S, more preferably N, O.

The term "3-8 membered carbon ring" used herein refers to a saturated, partially saturated or unsaturated monocyclic compound comprising 3-8 carbon atoms, including, for example, "3-7 membered carbon ring", "3-6 membered carbon ring", "4-7 membered carbon ring", "4-6 membered carbon ring", "5-6 membered carbon ring", etc. Its examples include, but are not limited to: cyclopropyl, cyclobutyl, cyclopentyl, cyclohexyl, cycloheptyl, cyclooctyl, cyclopentenyl, 1,3-cyclopentadienyl, cyclohexenyl, 1,4-cyclohexadienyl, cycloheptenyl, 1,4-cycloheptadienyl, cyclooctenyl, phenyl etc., preferably "5-6 membered saturated or partially saturated carbon ring".

The term "partially saturated" means that a ring moiety comprises at least one double bond or triple bond.

Examples of the Invention Also Provide Two Methods for Preparing the Compounds, but the Invention is not Limited to the Two Methods. The Schemes are as Follows.

Method I:

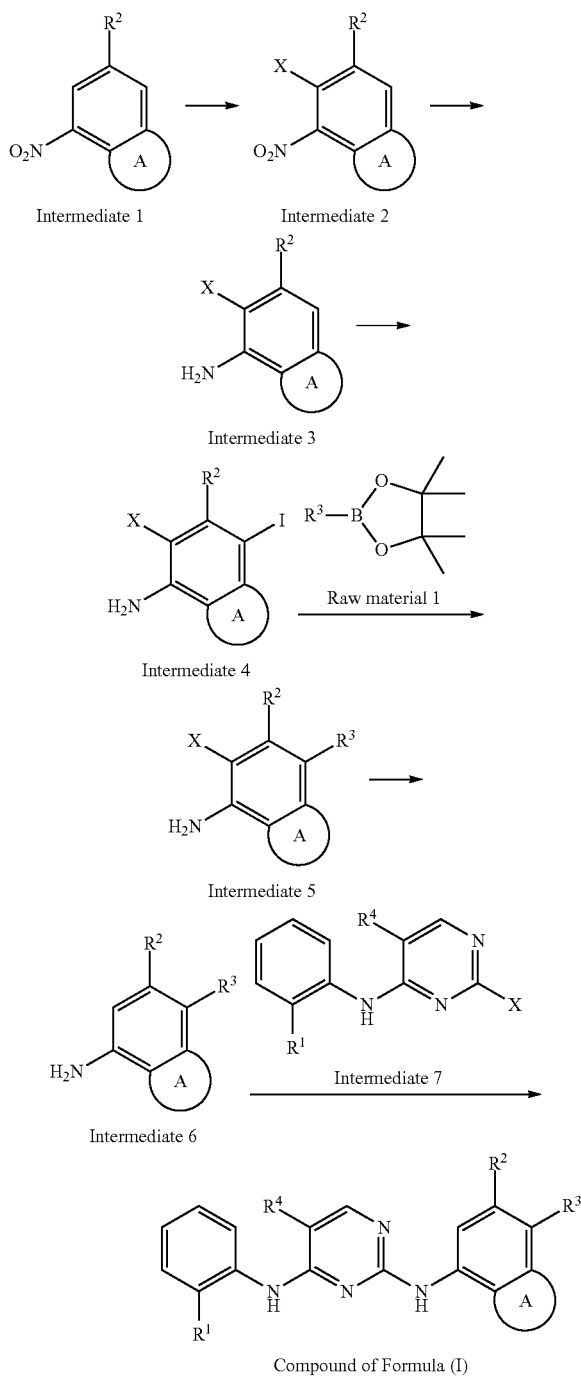

Step 1. Preparation of Intermediate 1
Intermediate 1 is either purchased or prepared.
Step 2. Preparation of Intermediate 2
Intermediate 1 is dissolved in a suitable solvent (e.g., N,N-dimethyl formamide), and N-bromobutanimide is added in a suitable amount. After heating (e.g., at 30-70° C.) and stirring (e.g., for 10-20 h), the resultant mixture is cooled to room temperature, and water is added to quench the reaction. After extraction with an organic solvent (e.g., ethyl acetate), concentration, and purification by a suitable method (e.g., silica gel column chromatography), Intermediate 2 is obtained.

Step 3. Preparation of Intermediate 3
Intermediate 2 is dissolved in a suitable solvent (e.g., ethanol), acetic acid is added, and reduced iron powder is added in batch. After heating (e.g., at 50-100° C.) and stirring (e.g., for 10-20 h), solids are removed by filtration, and water is added to quench the reaction. After extraction with an organic solvent (e.g., ethyl acetate), concentration, and purification by a suitable method (e.g., silica gel column chromatography), Intermediate 3 is obtained.

Step 4. Preparation of Intermediate 4
Intermediate 3 is dissolved in toluene and acetic acid. At room temperature, a suitable amount (e.g., 0.5-1.5 equivalent) of N-iodosuccinimideis added. After stirring (e.g., for 1-2 h), water is added to quench the reaction. After extraction with an organic solvent (e.g., ethyl acetate), concentration, and purification by a suitable method (e.g., silica gel column chromatography), Intermediate 4 is obtained.

Step 5. Preparation of Intermediate 5
Intermediate 4 and Raw material 1 are dissolved in a solvent (e.g., dioxane), metal Pd catalyst (e.g., [1,1'-bis(diphenylphosphino)ferrocene]dichloropalladium(II)) is added, and a suitable amount (e.g., 1-2 equivalent) of an inorganic base (e.g., potassium carbonate) is added. After reaction (e.g., for 1-3 h) under heating (e.g., at 50-100° C.) and the protection of nitrogen gas, suction filtration is carried out, and the filtrate is extracted with an organic solvent (e.g., ethyl acetate). The combined organic phase is purified by a suitable method (e.g., silica gel column chromatography) to obtain Intermediate 5.

Step 6. Preparation of Intermediate 6
Intermediate 5 is dissolved in a suitable solvent (e.g., methanol), Pd/C is added, and hydrogen gas is introduced at room temperature. After stirring (e.g., for 10-20 h), filtration, and concentration of the filtrate, Intermediate 6 is obtained.

Step 7. Preparation of Intermediate 7
N,N-dimethyl-2-nitrobenzenesulfonamide or 2-(isopropylsulfonyl)aniline is dissolved in a suitable solvent, and 2,4,5-trichloropyrimidine is added. After reaction at room temperature under stirring (e.g., for 16 h), water is added to quench the reaction. After extraction with an organic solvent (e.g., ethyl acetate), concentration, and purification by a suitable method (silica gel column chromatography), Intermediate 7 is obtained.

Step 8. Preparation of a Compound of Formula (I) According to the Invention
Intermediate 7 and Intermediate 6 are dissolved in a solvent (e.g., dioxane), metal Pd catalyst (e.g., [1,1'-bis(diphenylphosphino)ferrocene]dichloropalladium(II)) is added, and a suitable amount of an inorganic base (e.g., cesium carbonate) is added. After reaction (e.g., for 12-18 h) under heating (e.g., at 70-90° C.) and the protection of nitrogen gas, suction filtration is carried out, and the filtrate is concentrated. After purification by a suitable method (e.g., silica gel column chromatography), the compound of Formula (I) according to the invention is obtained.

Method II:

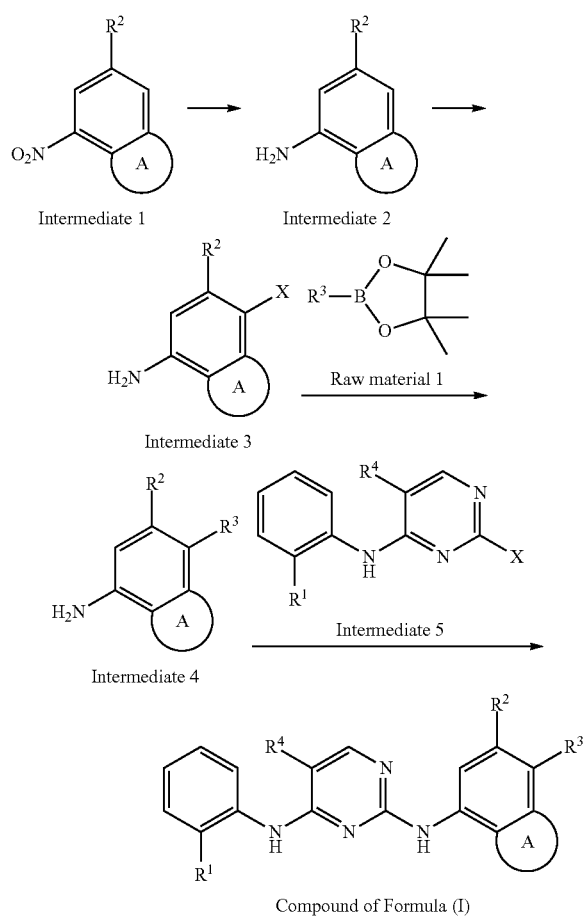

Step 1. Preparation of Intermediate 1
Intermediate 1 is purchase or prepared.
Step 2. Preparation of Intermediate 2
Intermediate 1 is dissolved in a suitable solvent (e.g., ethanol), and Pd/C is added. The reaction is carried out at room temperature under the protection of hydrogen (e.g., for 1-5 h). After the reaction, the solids are removed by filtration, and the filtrate is concentrated to obtain Intermediate 2.
Step 3. Preparation of Intermediate 3
Intermediate 2 is dissolved in a suitable solvent (e.g., acetic acid), and the temperature is decreased (e.g., to 5-20° C.). NIS is added. After reaction (e.g., for 30-50 min), acetic acid is removed. The resultant mixture is diluted by adding a solvent (e.g., ethyl acetate), washed with a sodium thiosulfate solution, washed with water, dried, filtrated, concentrated, and purified by a suitable method (e.g., silica gel column chromatography) to obtain Intermediate 3.
Step 4. Preparation of Intermediate 4
Intermediate 3 and Raw material 1 are dissolved in a solvent (e.g., dioxane), metal Pd catalyst (e.g., [1,1'-bis (diphenylphosphino)ferrocene]dichloropalladium(II)) is added, and a suitable amount (e.g., 1-2 equivalent) of an inorganic base (e.g., cesium carbonate) is added. After reaction (e.g., for 3-8 h) under heating (e.g., at 50-100° C.), an organic solvent (e.g., ethyl acetate) is added. After drying, concentration, and purification by a suitable method (e.g., silica gel column chromatography), Intermediate 4 is obtained.

Step 5. Preparation of Intermediate 5
Please refer to the step for preparation of Intermediate 7 in Method I.
Step 6. Preparation of a Compound of Formula (I) According to the Invention
Intermediate 4 and Intermediate 5 are dissolved in a solvent (e.g., tertiary amyl alcohol). After reaction (e.g., for 10-16 h) under heating (e.g., at 100° C.-130° C.), the resultant mixture is cooled, and an organic solvent (e.g., ethyl acetate) is added. The resultant mixture is washed with an alkaline solution (e.g., sodium bicarbonate), dried, concentrated, and purified by a suitable method (e.g., silica gel column chromatography) to obtain the compound of Formula (I) according to the invention.
In the schemes, $R^1$, $R^2$, $R^3$, $R^4$ and A ring have the same meanings as defined above. X represents fluorine atom, chlorine atom, bromine atom and iodine atom.
The term "stereoisomer" of the compound of Formula (I) used herein refers to enantiomer when the compound of Formula (I) has asymmetric carbon atom(s), refers to cis-trans-isomer when the compound has carbon-carbon double bond(s) or cyclic structure, and refers totautomer when the compound has ketone or oxime. All the enantiomers, diastereoisomers, racemes, cis-trans-isomers, tautomers, geometric isomers, and epimerides of the compound of Formula (I), and mixtures thereof fall into the scope of the invention.
If any compound of Formula (I) is obtained as raceme, the desired enantiomerically pure compound can be obtained by chiral separation method: chromatography using a chiral stationary phase (e.g., high pressure liquid preparative chromatography, super critical fluid chromatography). Chiral packing material includes, but is not limited to: Chiralcel OJ-H, Chiralpak AD-H, Chiralpak IA, Chiralpak AS-H.
A pharmaceutically acceptable salt of any compound of Formula (I) refers to a salt prepared by a pharmaceutically acceptable non-toxic base or acid, including a salt of organic acid, a salt of inorganic acid, a salt of organic base, and a salt of inorganic base.
In Examples, the invention further provides a pharmaceutical composition comprising the compound of Formula (I), or the pharmaceutically acceptable salt or stereoisomer thereof, and one or more pharmaceutically acceptable carrier and/or diluent, which may be prepared in any pharmaceutically acceptable dosage form. The pharmaceutical composition may be administered to a patient in need of this therapy by a suitable route, such as oral, parenteral, rectal, or intrapulmonary administration. When administered orally, the pharmaceutical composition may be prepared into a conventional solid preparation, such as tablet, capsule, pill, and granule; or may be prepared into an oral liquid preparation, such as oral solution, oral suspension, and syrup. When the pharmaceutical composition is prepared into an oral preparation, suitable fillers, binding agents, disintegrating agents, lubricants and the like may be added. When administered parenterally, the pharmaceutical composition may be prepared into an injection, including injectio, sterile powder for injection and concentrated solution for injection. When the pharmaceutical composition is prepared into an injection, conventional methods in pharmaceutical field may be used. When preparing an injection, additives may not be added, or suitable additives are added depending on the properties of drug. When administered rectally, the pharmaceutical composition may be prepared into a suppository, etc. When administered intrapulmonarily, the pharmaceutical composition may be prepared into inhalant, or spraying agent, etc.

In Examples, the invention further provide a pharmaceutical composition, comprising the compound of Formula (I), or the pharmaceutically acceptable salt or stereoisomer thereof, and one or more additional antitumor agent and/or immunosuppressor. The antitumor agent and/or immunosuppressor is anantimetabolite, selected from the group consisting of capecitabine, gemcitabine and pemetrexed disodium; or the antitumor agent and/or immunosuppressor is a growth factor inhibitor, selected from the group consisting of pazopanib, imatinib, erlotinib, lapatinib, gefitinib and vandetanib; or the antitumor agent and/or immunosuppressor is an antibody, selected from the group consisting of herceptin and bevacizumab; or the antitumor agent and/or immunosuppressor is amitotic inhibitor, selected from the group consisting of paclitaxel, vinorelbine, docetaxel and doxorubicin; or the antitumor agents and/or immunosuppressor is an antitumor hormone, selected from the group consisting of letrozole, tamoxifen, fulvestrant, flutamide and triptorelin; or the antitumor agent and/or immunosuppressor is an alkylating agent, selected from the group consisting of cyclophosphamide, nitrogen mustard, melphalan, chlorambucil, carmustine and temozolomide; or the antitumor agent and/or immunosuppressor is a metallic platinum, selected from the group consisting of carboplatin, cisplatin and oxaliplatin; or the antitumor agent and/or immunosuppressor is an immunosuppressor, selected from the group consisting of everolimus, sirolimus and temsirolimus; or the antitumor agent and/or immunosuppressor is a purine analog, selected from the group consisting of 6-mercaptopurine, 6-thioguanineandazathioprine; or the antitumor agent and/or immunosuppressor is anantibiotic, selected from the group consisting of Actinomycin D, daunorubicin, doxorubicin, mitoxantrone, bleomycin and plicamycin; or the antitumor agent and/or immunosuppressor is a platinum complex, selected from the group consisting of cisplatin and carboplatin; or the antitumor agent and/or immunosuppressor is an adrenocortical inhibitor, selected from aminoglutethimide; or the antitumor agent and/or immunosuppressor is an enzyme inhibitor, selected from the group consisting of cytarabine, methotrexate, hydroxyurea, hydroxycamptothecin, camptothecin, topotecan and irinotecan.

In Examples, the invention also provides a use of the compound of Formula (I), or the pharmaceutically acceptable salt or stereoisomer thereof, in the manufacture of a medicament for use in the treatment and/or prevention of an ALK-mediated cancer or non-cancer related disease, wherein the cancer related disease is selected from the group consisting of brain carcinoma, lung cancer, non-small cell lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, hepatoblastoma, papillary renal cell carcinoma, head neck squamous cell carcinoma, nephroblastoma, renal carcinoma, esophageal adenocarcinoma, esophageal squamous cancer, non-Hodgkin lymphoma, central nervous system tumor, female reproductive duct cancer, cancer in situ, lymphoma, neurofibromatosis, thyroid cancer, osteocarcinoma, skin cancer, cerebral cancer, colon cancer, testiculus cancer, small cell lung cancer, gastrointestinal stromal tumor, prostate tumor, mast cell tumor, multiple myeloma, melanoma, glioma, astrocytoma, neuroblastoma, sarcoma and neuroglioma; the non-cancer related disease is selected from benign hyperplasia of skin and prostate.

In Examples, the invention also provides the compound of Formula (I), or the pharmaceutically acceptable salt or stereoisomer thereof, or the pharmaceutical composition, for use in the treatment and/or prevention of an ALK-mediated cancer or non-cancer related disease, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin and prostate.

In Examples, the invention also provides a method for treating and/or preventing an ALK-mediated cancer or non-cancer related disease, comprising administering to a patient in need thereof an effective amount of the compound of Formula (I), or the pharmaceutically acceptable salt or stereoisomer thereof, or the pharmaceutical composition, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin and prostate.

The Compound Provided in Examples of the Invention has the Following Advantages.

(1) The compound of Formula (I), or a pharmaceutically acceptable salt or a stereoisomer thereof according to the invention has excellent ALK/ROS1 inhibitory activity.

(2) The compound of Formula (I), or a pharmaceutically acceptable salt or a stereoisomer thereof according to the invention exhibits good biostability, a longer lasting effect, and high bioavailability.

(3) The preparation processes of the compounds as provided in Examples of the invention are simple, and the pharmaceutical products thus obtained have high purity and stable quality, and are easily produced in industry in a large scale.

(4) The compound of Formula (I), or a pharmaceutically acceptable salt or a stereoisomer thereof according to the invention has good inhibitory activity in drug-resistant cells such as BaF3(ALK-F1174L), BaF3(ALK-C1156Y), and BaF3(ALK-L1196M).

The following experiments are provided to further illustrate the beneficial effects of the compounds provided in Examples of the invention, but it shall not be understood that the compounds provided in Examples of the invention only have the following beneficial effects.

The meanings of the abbreviations in the following experiments are described as follows.
DMSO: Dimethyl sulfoxide
DTT: DL-Dithiothreitol
SEB: Supplement Enzymatic buffer
ATP: Adenosine Triphosphate
ALK: Anaplastic Lymphoma Kinase
SA-XL665: Streptavidin-XL665
HEPES: 4-(2-hydroxyethyl)piperazine-1-ethanesulfonic acid
Brij-35: polyethylene glycol dodecyl ether
EDTA: ethylenediaminetetraacetic acid
"×" in 2.5×, 5×, 10×: fold
The full names in English are obtained from the instructions of kit.

Experimental Example 1 Assay on In Vitro ALK Kinase-Inhibiting Activity of the Compounds Provided in Examples of the Invention Test compounds: Compounds 1, 2, 3 and 4 provided in Examples of the invention, the chemical names and preparation methods of which can be found in the preparation examples.
Control agent: Ceritinib, lab-made (prepared by reference to the method in Publication WO2008/073687A2).
Experimental Method
Preparation of ALK Kinase Buffer:
A suitable amount of a stock solution of $MgCl_2$ at a concentration of 1000 mM, a suitable amount of a stock solution of SEB at a concentration of 2500 nM, a suitable amount of a stock solution of DTT at a concentration of 100 mM, and a suitable amount of 5×enzyme buffer were added to ultrapure water to reach a final concentration of: 5 mM, 25 nM, 1 mM, and 1×enzyme buffer, respectively. The resultant mixture was mixed homogeneously, for later usage.
Preparation of 2.5×Test Compound Solutions:
Preparation of a stock solution of control agent at a concentration of 1 mM: 1.48 mg control agent was weighed, and was dissolved by adding a suitable amount of DMSO. The resultant mixture was mixed homogeneously, for later usage.
Preparation of a stock solution of compound at a concentration of 1 mM: a suitable amount of compound (please see the following table for sample weight) was weighed, and dissolved by adding a suitable amount of DMSO. The resultant mixture was mixed homogeneously, for later usage.

| | Test compound | | | |
|---|---|---|---|---|
| | Compound 1 | Compound 2 | Compound 3 | Compound 4 |
| Sample weight (mg) | 1.58 | 1.44 | 1.72 | 1.58 |

Each of the 1 mM stock solutions was diluted with DMSO to a 200 μM solution, which was used as initial solution. Each of said initial solutions was 3-fold diluted with DMSO to prepare a series of solutions of different concentrations, and then the solution of each concentration was diluted with the ALK kinase buffer by 80 folds to prepare a 2.5×test compound solution. The concentrations were: 2500 nM, 833.33 nM, 277.78 nM, 92.59 nM, 30.86 nM, 10.29 nM, 3.43 nM, 1.14 nM, 0.38 nM, 0.13 nM, 0.04 nM.

Preparation of Other Reagents:
5×ALK kinase solution, 5×substrate solution, and 5×ATP solution, were prepared by using the ALK kinase buffer, for later usage.
ALK Enzymatic Reaction:
1) 4 μL 2.5× test compound solution and 2 μL 5×ALK kinase solution were added to the corresponding wells in a 384-well plate, respectively, and incubated at 25° C. for 10 min.
2) To the corresponding wells, 2 μL 5× substrate solution and 2 μL 5×ATP solution were further added to start the enzymatic reaction, and incubation was performed at 25° C. for 30 min.
Enzymatic Assay
Detection buffer was used to prepare SA-XL665 at a desired concentration, which was then mixed homogeneously with the same volume of tyrosine kinase antibody. To the corresponding wells, 10 μL said antibody solution was added, and the reaction was stopped. Incubation was performed at 25° C. for 1 h.
The plate was read by Microplate Readerat 665 nm/615 nm.
$IC_{50}$: Inhibition rate (%)=(maximal value-sample value)/(maximal value-minimal value)×100, wherein Graph prism software was used in curve fitting to get $IC_{50}$ value.
Maximal value: positive control without addition of compound; minimal value: negative control without addition of enzyme.
Experimental Results and Conclusion:

TABLE 1

In vitro enzyme-inhibiting activity of the compounds provided in Examples of the invention

| Test compound | ALK enzyme-inhibiting activity $IC_{50}$ (nM) |
|---|---|
| Ceritinib | 2.7 |
| Compound 1 | 0.2 |
| Compound 2 | 1.7 |
| Compound 3 | 0.6 |
| Compound 4 | 0.9 |

As seen from Table 1, the compounds provided in Examples of the invention have good inhibitory activity on ALK kinase, can be used in the treatment of kinase-related diseases, particularly ALK kinase-mediated symptoms or conditions, and have important clinical significance.

Experimental Example 2 Assay on In Vitro ALK Kinase-Inhibiting Activity of the Compounds Provided in Examples of the Invention Test compounds: Compounds 5, 6 and 8 provided in Examples of the invention, the chemical names and preparation methods of which can be found in the preparation examples.
Control agent: Ceritinib, lab-made (prepared by reference to the method in Publication WO2008/073687A2).
Experimental method: Measurement of ALK kinase inhibitory activity by Caliper Mobility Shift assay.
1. Preparation of 1-Fold Kinase Buffer
To pH7.5HEPES, Brij-35 at a concentration of 30%, a stock solution of $MgCl_2$ at a concentration of 1M, and a stock solution of DTT at a concentration of 1M, ultrapure water was added and mixed homogeneously until HEPES was at a final concentration of 50 mM, Brij-35 was at a final concentration of 0.0015%, MgCl$_2$ was at a final concentration of 10 mM, and DTT was at a final concentration of 2 mM.

2. Preparation of Stop Solution

To a stock solution of Coating Reagent #3a concentration of 4% (a coating solution provided in the 12-sipper chip used in Caliper device), a stock solution of pH7.5HEPES at a concentration of 1000 mM, a stock solution of EDTA at a concentration of 0.5 M, and a stock solution of Brij-35 at a concentration of 30%, ultrapure water was added and mixed homogeneously until Coating Reagent #3 was at a final concentration of 0.2%, HEPES was at a final concentration of 100 mM, EDTA was at a final concentration of 50 mM, and Brij-35 was at a final concentration of 0.015%.

3. Preparation of 5-Fold Test Compound Solutions:

Preparation of a DMSO stock solution of test compound: a suitable amount of compound (please see the following table for sample weight) was weighed, and dissolved by adding a suitable amount of DMSO. The resultant mixture was mixed homogeneously, for later usage.

| | Test compound | | | |
|---|---|---|---|---|
| | Ceritinib | Compound 5 | Compound 6 | Compound 8 |
| Sample weight (mg) | 2.28 | 2.06 | 2.14 | 2.05 |

Said DMSO stock solution of test compound was diluted with DMSO to a solution at a concentration of 50 µM, which was used as initial solution. Said initial solution was subjected to 4-fold gradient dilution with DMSO, and the solution at each concentration was 10-fold diluted with 1-fold kinase buffer to prepare a 5-fold test compound solution.

4. Preparation of Other Reagents:

2.5×ALK kinase solution and 2.5× polypeptide solution were prepared by using the 1-fold kinase buffer, for later usage.

5. Enzymatic Reaction 1) 5 µL 5-fold test compound solution and 10 µL 2.5-fold kinase solution were added to the corresponding wells in a 384-well plate, and incubated at room temperature for 10 min.

2) To the corresponding wells, 10 µL 2.5-fold polypeptide solution was added until the test compound was at a final concentration of 1000 nM, 250 nM, 63 nM, 16 nM, 4 nM, 1 nM, 0.2 nM, 0.1 nM, 0.02 nM and 0.004 nM, respectively. The enzymatic reaction was started, and the incubation was performed at 28° C. for 1 h.

6. Enzymatic Assay

To the corresponding wells, 25 µL stop solution was added to stop the reaction. Data was read by Caliper device, and the inhibition rate was calculated by the data, Inhibition rate (%)=(maximal value−sample value)/(maximal value−minimal value)×100, wherein XLFIT software was used in curve fitting to get IC$_{50}$ value.

Maximal value: positive control without addition of test compound; minimal value: negative control without addition of enzyme.

Experimental Results and Conclusion:

TABLE 2

In vitro enzyme-inhibiting activity of the compounds provided in Examples of the invention

| Test compound | ALK enzyme-inhibiting activity IC$_{50}$ (nM) |
|---|---|
| Ceritinib | 3.9 |
| Compound 5 | 0.36 |
| Compound 6 | 0.45 |
| Compound 8 | 0.54 |

As seen from Table 2, the compounds provided in Examples of the invention have good inhibitory activity on ALK kinase, can be used in the treatment of kinase-related diseases, particularly ALK kinase-mediated symptoms or conditions, and have important clinical significance.

Experimental Example 3 Assay on In Vitro ROS1 Kinase-Inhibiting Activity of the Compounds Provided in Examples of the Invention Test compounds: Compounds 1, 2, 3, 4 and 8 provided in Examples of the invention, the chemical names and preparation methods of which can be found in the preparation examples.

Experimental method: Measurement of inhibitory activity on ROS1 kinase by Caliper Mobility Shift assay.

1. Preparation of 1-Fold Kinase Buffer

To HEPES of pH7.5, Brij-35 at a concentration of 30%, a stock solution of MgCl$_2$ at a concentration of 1M, and a stock solution of DTT at a concentration of 1M, ultrapure water was added and was mixed homogeneously until HEPES was at a final concentration of 50 mM, Brij-35 was at a final concentration of 0.0015%, MgCl$_2$ was at a final concentration of 10 mM, and DTT was at a final concentration of 2 mM.

2. Preparation of Stop Solution

To a stock solution of Coating Reagent #3 at a concentration of 4% (a coating solution provided in the 12-sipper chip used in Caliper device), a stock solution of HEPES of pH7.5 at a concentration of 1000 mM, a stock solution of EDTA at a concentration of 0.5 M, and a stock solution of Brij-35 at a concentration of 30%, ultrapure water was added and mixed homogeneously until Coating Reagent #3 was at a final concentration of 0.2%, HEPES was at a final concentration of 100 mM, EDTA was at a final concentration of 50 mM, and Brij-35 was at a final concentration of 0.015%.

3. Preparation of 5-Fold Test Compound Solutions:

Preparation of a DMSO stock solution of test compound: a suitable amount of compound (please see the following table for sample weight) was weighed, and dissolved by adding a suitable amount of DMSO. The resultant mixture was mixed homogeneously, for later usage.

| Test compound | Ceritinib | Compound 1 | Compound 2 | Compound 3 | Compound 4 | Compound 8 |
|---|---|---|---|---|---|---|
| Sample weight (mg) | 2.28 | 2.04 | 2.02 | 1.98 | 2.1 | 1.83 |

Said DMSO stock solution of test compound was diluted with DMSO to a solution at a concentration of 50 µM, which was used as initial solution. Said initial solution was subjected to 4-fold gradient dilution with DMSO, and the solution at each concentration was 10-fold diluted with 1-fold kinase buffer to prepare a 5-fold test compound solution.

4. Preparation of Other Reagents 2.5×ROS1 kinase solution and 2.5×polypeptide solution were prepared by using the 1-fold kinase buffer, for later usage.

5. Enzymatic Reaction 1) 5 μL 5-fold test compound solution and 10 μL 2.5-fold kinase solution were added to the corresponding wells in a 384-well plate, and incubated at room temperature for 10 min.

2) To the corresponding wells, 10 μL 2.5-fold polypeptide solution was added until the test compound was at a final concentration of 1000 nM, 250 nM, 63 nM, 16 nM, 4 nM, 1 nM, 0.2 nM, 0.1 nM, 0.02 nM, and 0.004 nM, respectively. The enzymatic reaction was started, and the incubation was performed at 28° C.

6. Enzymatic Assay

To the corresponding wells, 25 μL stop solution was added to stop the reaction. Data was read by Caliper device, and the inhibition rate was calculated by the data, Inhibition rate (%)=(maximal value-sample value)/(maximal value-minimal value)×100, wherein XLFIT software was used in curve fitting to get $IC_{50}$ value.

Maximal value: positive control without addition of compound; minimal value: negative control without addition of enzyme.

Experimental Results and Conclusion:

The experimental results show that the compounds provided in Examples of the invention have an inhibitory activity of less than 1 nM for ROS1 kinase, while Ceritinib has an inhibitory activity of greater than 10 nM for ROS1 kinase, indicating that compared to Ceritinib, the compounds of the invention have a better ROS1 kinase inhibitory activity, and are superior in the treatment of kinase associated diseases.

Experimental Example 4 Assay on In Vitro Cell Activity of the Compounds Provided in Examples of the Invention Test compounds: Compounds 1-6 and 8 provided in Examples of the invention, the chemical names and preparation methods of which can be found in the preparation examples.

Control agent: Ceritinib, lab-made (prepared by reference to the method in Publication WO2008/073687A2), the formula of which is shown in the Background.

The meanings of abbreviations in the following experiments are described as follows.

rpm: revolutions per min;
DMSO: dimethyl sulfoxide;
MTS: 3-(4,5-dimethylthiazol-2-yl)-2,5-diphenyl-2H-tetrazoliumbromide;
RPMI1640: 1640 medium (RPMI: Roswell Park Memorial Institute);
"×" in 500×, 1000×, 10×: fold.

Experimental Method (I) NCI-H3122, Karpas-299Cell:
(1) Cell Preparation:
The cells were cultured to a fusion degree of 80% in RPMI-1640 medium containing 10% fetal bovine serum, 100 U/ml penicillin and 100 mg/ml streptomycin, in a 37° C., 5% $CO_2$ incubator, for later usage.

(2) Cell Seeding:
Cells were digested with pancreatin. After centrifugation at 1000 rpm for 4 min, the supernatant was removed. The cells were re-suspended in RPMI-1640 medium containing 2.5% fetal bovine serum, and the cell density was adjusted. The cell suspension (90 μL) was seeded to a 96-well plate to obtain a final cell density of 3000 cells/well; and then cultured in a 5% $CO_2$, 37° C. incubator for 24 h.

(3) Addition of Test Compound:
(3.1) Preparation of Test Compound Solutions:
Preparation of test compound solutions: a suitable amount of test compound (please see the following table for sample weight) was weighed, and diluted gradiently with DMSO to prepare a series of stock solutions of different concentrations (1000×test compound solution). Each of said stock solutions was further diluted by 100 folds with medium to obtain a 10×test compound solution. The resulting solutions (10 μL) each were added to the corresponding wells in a 96-well plate to obtain the test compound solutions at a final concentration of: 10 μM, 2.5 μM, 625 nM, 156 nM, 39 nM, 9.8 nM, and 2.5 nM, respectively.

| Compound | Ceritinib | 1 | 2 | 3 | 4 | 5 | 6 | 8 |
|---|---|---|---|---|---|---|---|---|
| Sample weight (mg) | 3.02 | 1.91 | 2.06 | 1.72 | 2.11 | 2.00 | 2.07 | 2.16 |

(3.2) Control Wells:
Solvent control: 0.1% DMSO.
Cell control: cell seeding only, with no addition of compound.
Blank control: medium, for zero setting in an instrument.
(3.3) The 96-well plate was cultured in a 37° C., 5% $CO_2$ incubator for 72h.

(4) Detection:
MTS detection:
① The reagents in CellTiter 96®AQueous One Solution Cell Proliferation Assay (MTS) were placed at room temperature for 90 min.
② To each test well in the 96-well plate, 20 μL CellTiter 96® A Queous One Solution reagent was added.
③ The 96-well plate was cultured in a 37° C., 5% $CO_2$ incubator for 40 min.
④ The results were read by Microplate Reader at 490 nm.
(5) Results
$IC_{50}$ calculation: cell survival rate (%)=($OD_{sample\ value}$−$OD_{blank\ value}$)/($OD_{maximal\ value}$−$OD_{blank\ value}$)×100, wherein Graph prisim software is used in curve fitting to get $IC_{50}$ value.

$OD_{maximal\ value}$: cell control with the addition of solvent and no compound, $OD_{blank\ value}$: blank control value.

(II) Nci-H2228Cell:
(1) Cell Preparation:
The cells were cultured to a fusion degree of 80% in RPMI-1640medium containing 10% fetal bovine serum, in a 5% $CO_2$, 37° C. incubator, for later usage.

(2) Cell Seeding:
Cells were digested with pancreatin. After centrifugation at 1000 rpm for 4 min, the supernatant was removed. The cells were re-suspended in RPMI-1640 medium containing 2.5% fetal bovine serum, and the cell density was adjusted to $2\times10^4$ cells/mL. The cell suspension (100 μL) was seeded to a 96-well plate to obtain a final cell density of 2000 cells/well.

(3) Addition of Test Compound:

(3.1) Preparation of test compound solutions: a suitable amount of test compound (please see the following table for sample weight) was weighed, and dissolved by adding a suitable amount of DMSO. The resultant mixture was mixed homogeneously, and diluted gradiently with DMSO to prepare a series of solutions of different concentrations, for later usage.

| Compound | Ceritinib | 1 | 2 | 3 | 4 | 5 | 6 | 8 |
|---|---|---|---|---|---|---|---|---|
| Sample weight (mg) | 2.97 | 2.52 | 1.93 | 1.95 | 2.15 | 2.01 | / | / |

99 μL medium was added to each well in the 96-well plate, and 1 μL said test compound solution of a different concentration was then added to the corresponding well, so that the compounds and the control agent were at a final concentration of: 10000 nM, 2500 nM, 625 nM, 156.25 nM, 39.06 nM, 9.77 nM, 2.44 nM, and 0.61 nM, respectively.

(3.2) Control Wells:

Solvent control: 0.5% DMSO.

Cell control: cell seeding only, with no addition of compound.

Blank control: medium, for zero setting in an instrument.

(3.3) The 96-well plate was cultured in a 37° C., 5% $CO_2$ incubator for 96 h.

(4) Detection:

CTG detection:

① 80 μL medium was removed from each well in the 96-well plate, and the plate was placed at room temperature for 30 min.

② 60 μL CellTiter-Glo® reagent was added to each test well in the 96-well plate.

③ The 96-well plate was shaken for 2 min in dark to mix the mixture homogeneously in a microplate shaker, so as to lyse the cells.

④ The 96-well plate was incubated in dark at room temperature for 10 min, to keep the light signal value stable.

⑤ The results were read by Microplate Reader in luminescence mode.

5. Results $IC_{50}$ calculation: cell inhibition rate (%)=$(OD_{maximal\ value}-OD_{compound})/(OD_{maximal\ value}-OD_{blank\ value})\times 100$, wherein Graph prisim software is used in curve fitting to get $IC_{50}$ value.

$OD_{maximal\ value}$: cell control with the addition of solvent and no compound, $OD_{blank\ value}$: medium blank control.

Experimental Results

TABLE 3

The cell-inhibiting activity of the compounds provided in Examples of the invention

| Test compound | $IC_{50}$ (nM) | | |
|---|---|---|---|
| | NCI-H3122 | Karpas-299 | NCI-H2228 |
| Ceritinib | 138.1 | 29.98 | 48.06 |
| Compound 1 | 10.94 | 0.7 | 3.206 |
| Compound 2 | 4.18 | 7.656 | 5.469 |
| Compound 3 | 43.23 | 0.164 | 1.715 |
| Compound 4 | 130.4 | 0.71 | 15.11 |
| Compound 5 | 25.15 | 5.36 | 7.406 |
| Compound 6 | 61.72 | 9.916 | / |
| Compound 8 | 16.05 | 5.182 | / |

Note:
"/" represents no value detected.

As seen from Table 3, the compounds provided in Examples of the invention have good inhibitory activity against cells NCI-H3122, Karpas-299 and NCI-H2228, can be used in the treatment of ALK kinase-mediated symptoms or conditions, and have important clinical significance.

Experimental Example 5 Assay on In Vitro Cell Activity of the Compounds Provided in Examples of the Invention The compounds provided in Examples of the invention have good inhibitory activity against BaF3(ALK-F1174L), BaF3(ALK-C1156Y), BaF3(ALK-L1196M), and are superior to Ceritinib, indicating that the compounds provided in Examples of the invention have a strong inhibitory effect on ALK drug-resistant cells, and have important clinical significance in the treatment of diseases caused by ALK mutation.

Experimental Example 6 Assay on Pharmacokinetics of the Compounds Provided in Examples of the Invention in Rat Test compounds: Compound 4, lab-made, the chemical name and preparation method of which can be found in the preparation example.

Internal standard: Alectinib, lab-made (prepared by reference to the method in Patent CN102459172A).

I. Preparation of Test Compound Colutions

1. Oral Administration (Po)

0.1% Tween 80+2% HPC: HPC (hydroxypropyl cellulose) (20 g) was weighed, and was added slowly to purified water (1000 mL) under stirring; Tween 80 (1 mL) was then added, and the resultant mixture was stirred until a clear solution was obtained, i.e. a blank solvent of 0.1% Tween 80+2% HPC.

A suitable amount of test compound (please see the following table for sample weight) was weighed, and said prepared solvent was added. The resultant mixture was placed in a tissue grinder, and was dispersed homogeneously at a rotation speed of 1000 r/min to get a solution for intragastric administration.

| | Compound Compound 4 |
|---|---|
| Sample weight (mg) | 6.10 |

2. Intravenous Administration (Iv)

Preparation of 40% HP-β-CD: 4.0 g HP-β-CD (Hydroxypropyl-β-Cyclodextrin) was weighed, and was dissolved ultrasonically by adding 5 mL purified water. Purified water was added to a final volume of 10 mL, to obtain 40% HP-β-CD solution. A suitable amount of test compound (please see the following table for sample weight) was weighed, and dissolved ultrasonically by adding DMSO (DMSOvolume=5% total volume). 40% HP-β-CD solution (40% HP-β-CD volume=20% total volume) was added. The resultant mixture was mixed homogeneously under vortexing, and placed in a 50° C. thermostatic water bath tank for 20 min. Sterile water for injection (volume of sterile water for injection=75% total volume) was then added. After vortexing, mixing homogeneously, and passing through a 0.22 μM filter membrane, a clear and transparent solution for intravenous injection was obtained.

|  | Compound No. Compound 4 |
|---|---|
| Sample weight (mg) | 3.05 |

The test compound solutions were administered by the methods listed in the following table:

| Test compounds | Cases of experimental animal | Administration route | Administration dose (mg/kg) | Administration concentration (mg/mL) | Administration volume (mL/kg) |
|---|---|---|---|---|---|
| Compound 4 | 3 | iv | 2 | 1.0 | 2 |
|  | 3 | po | 5 | 1.0 | 5 |

II. Experimental Method
1. Blood Collection Time Point:
iv: 0.083 h, 0.25 h, 0.5 h, 1 h, 2 h, 4 h, 6 h, 8 h, 24 h after administration.
po: 0.167 h, 0.5 h, 1 h, 2 h, 4 h, 6 h, 8 h, 24 h after administration.
About 100 μL whole blood was collected from caudal vein at each time point, added to an anticoagulation tube containing $K_2$EDTA, and centrifuged at 8000 r/min for 6 min at a low temperature to separate plasma; the plasma was stored in refrigerator at −80° C.
2. Plasma Sample Analysis:
Protein precipitation method: to 30 μL plasma, 200 μL internal standard (acetonitrile solution containing 50 ng/mL Alectinib) was added; the resultant mixture was vortexed at 1000 r/min for 10 min, and then centrifuged at 4000 r/min for 20 min; to 100 μL supernatant, 100 μL water was added; the resultant mixture was mixed homogeneously under vortexing and analyzed by LC-MS/MS.
III. Experimental Results
Compound 4 has a bioavailability of 30%-50%, indicating that the compounds provided in Examples of the invention have good pharmacokinetic property in rat, have good drugability and are promising in clinical development.
The contents of the invention are further described in detail by the following embodiments in the form of Examples. However, it should not be understood that the subject matters of the invention are merely limited to the following Examples. All the technical solutions that are carried out based on the contents of the invention belong to the scope of the invention.

The meanings of the following abbreviations are described as follows:
DMF: N,N-dimethyl formamide
NBS: N-bromosuccinimide
NIS: N-iodosuccinimide
X-phos: 2-dicyclohexylphosphino-2',4',6'-triisopropylbiphenyl
Boc: t-butyloxy carbonyl
TFA: trifluoroacetic acid
THF: tetrahydrofuran
Tf: trifluoromethanesulfonyl
DCM: dichloromethane
DMSO: dimethyl sulfoxide
EA: ethyl acetate
PE: petroleum ether
DEAD: diethyl azodicarboxylate Example 1 Preparation of 5-chloro-$N^4$-(2-(isopropylsulfonyl)phenyl)-$N^2$-(6-methyl-7-(piperidin-4-yl)benzo[d][1,3]dioxol-4-yl)pyrimidine-2,4-diamine (Compound 1)

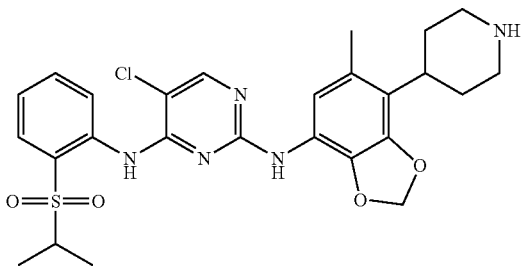 [SMILES: Cc1cc(Nc2ncc(Cl)c(Nc3ccccc3S(=O)(=O)C(C)C)n2)c2c(c1C1CCNCC1)OCO2]

(1) Preparation of 6-methyl-4-nitrobenzo[d][1,3]dioxole

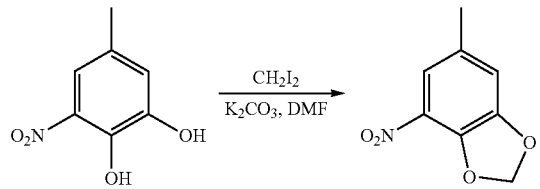

5-Methyl-3-nitrobenzene-1,2-diol (10 g, 59.1 mmol) was dissolved in DMF (200 mL), and diiodomethane (31.6 g, 118 mmol) and potassium carbonate (24.4 g, 177 mmol) were added. The resultant mixture was heated to 55° C. and reacted for 16 h under stirring. After the reaction, the resultant mixture was cooled to room temperature, and 300 mL water was added. After extraction with ethyl acetate (200 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=30:1) to obtain the product (5.1 g, yield: 48%).

(2) Preparation of 5-bromo-6-methyl-4-nitrobenzo[d][1,3]dioxole

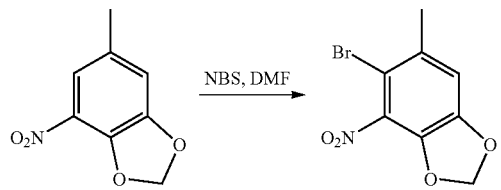

6-Methyl-4-nitrobenzo[d][1,3]dioxole (5.1 g, 28.2 mmol) was dissolved in DMF (100 mL), and NBS (10 g, 56.2 mmol) was added. The resultant mixture was heated to 55° C. and reacted for 16 h under stirring. After the reaction, the resultant mixture was cooled to room temperature, and 200 mL water was added. After extraction with ethyl acetate (200 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=30:1) to obtain the product (5.0 g, yield: 68%).

(3) Preparation of 5-bromo-6-methylbenzo[d][1,3]dioxol-4-amine

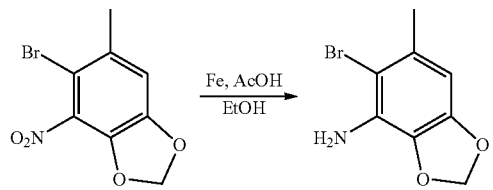

5-Bromo-6-methyl-4-nitrobenzo[d][1,3]dioxole (5.0 g, 19.2 mmol) was dissolved in ethanol (100 mL), and acetic acid (20 mL) and iron powder (5.4 g, 96.7 mmol) were added. The resultant mixture was heated to 80° C. and reacted under stirring for 16 h. After the reaction, the resultant mixture was cooled to room temperature, and filtrated. 200 mL water was added to the filtrate. After extraction with ethyl acetate (200 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=20:1) to obtain the product (2.9 g, yield: 66%).

(4) Preparation of 5-bromo-7-iodo-6-methylbenzo[d][1,3]dioxol-4-amine

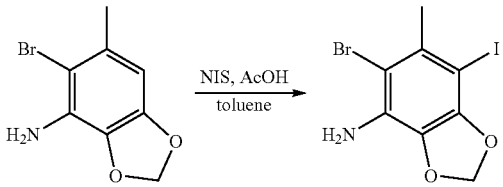

5-Bromo-6-methylbenzo[d][1,3]dioxol-4-amine (2.9 g, 12.6 mmol) was dissolved in toluene (40 mL), and NIS (4.26 g, 18.9 mmol) and acetic acid (1.0 mL) were added. The resultant mixture was reacted at room temperature under stirring for 2 h. After the reaction, 50 mL ice water was added. After extraction with ethyl acetate (100 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=20:1) to obtain the product (2.4 g, yield: 53%).

(5) Preparation of tert-butyl4-(7-amino-6-bromo-5-methylbenzo[d][1,3]dioxol-4-yl)-3,6-dihydro pyridine-1(2H)-carboxylate

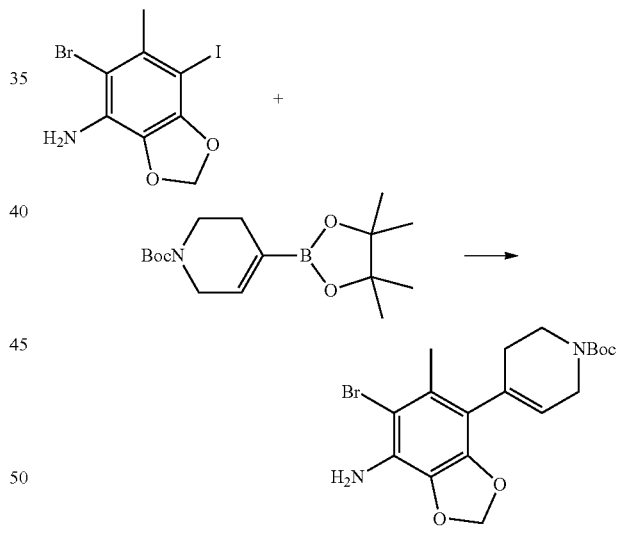

Tert-butyl4-(4,4,5,5-tetramethyl-1,3,2-dioxaborolan-2-yl)-3,6-dihydropyridine-1(2H)-carboxylate (2.5 g, 8.1 mmol) and 5-bromo-7-iodo-6-methylbenzo[d][1,3]dioxol-4-amine (2.4 g, 6.7 mmol) were dissolved in a mixed solvent of 1,4-dioxane (50 mL) and water (20 mL). To the system, potassium carbonate (2.77 g, 20.0 mmol) and 1,1'-bis (diphenylphosphino)ferrocene-palladium(II) dichloride dichloromethane complex (493 mg, 0.6 mmol) were added. Under the protection of nitrogen gas, the resultant mixture was reacted at 80° C. under stirring for 2 h. After the reaction, the resultant mixture was cooled to room temperature, and 100 mL water was added. After extraction with ethyl acetate (100 mL×2), the organic phases were combined, dried with anhydrous sodium sulphate, filtrated, and concentrated to obtain the crude product. After purification by silica gel column chromatography (petroleum ether:ethyl acetate=10:1), the product (1.3 g, yield: 47%) was obtained.

(6) Preparation of tert-butyl 4-(7-amino-5-methyl-benzo[d][1,3]dioxol-4-yl)piperidin-1-carboxylate

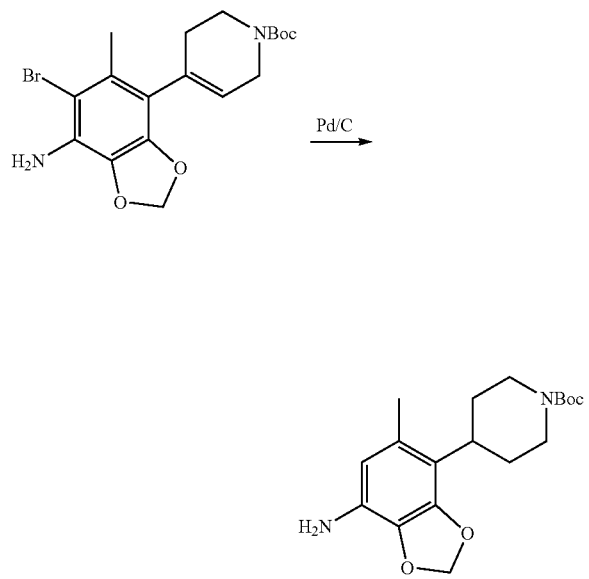

Tert-butyl4-(7-amino-6-bromo-5-methylbenzo[d][1,3]dioxol-4-yl)-3,6-dihydropyridine-1(2H)-carboxylate (1.3 g, 3.16 mmol) was dissolved in methanol (50 mL). Under the protection of nitrogen gas, Pd/C (1.3 g) was added to the system. At the atmosphere of hydrogen gas, the resultant mixture was reacted at room temperature under stirring for 16 h. After the reaction, the resultant mixture was filtrated and concentrated to obtain the product (800 mg, yield: 76%).

(7) Preparation of tert-butyl 4-(7-((5-chloro-4-((2-(isopropylsulfonyl)phenyl)amino)pyrimidin-2-yl)amino)-5-methylbenzo[d][1,3]dioxol-4-yl)piperidin-1-carboxylate

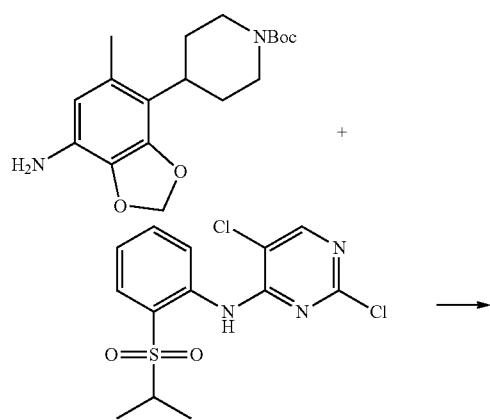

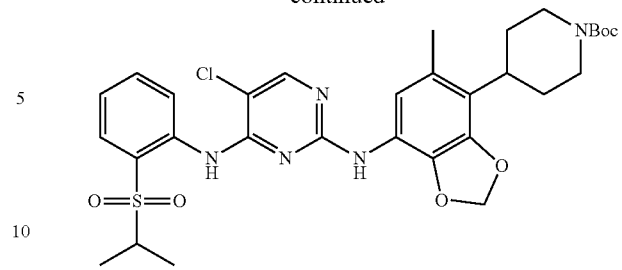

Tert-butyl 4-(7-amino-5-methylbenzo[d][1,3]dioxol-4-yl)piperidin-1-carboxylate (200 mg, 0.6 mmol) and 2,5-dichloro-N-(2-(isopropylsulfonyl)phenyl)pyrimidin-4-amine (prepared by the method described in Step (11) of Example 5, 168 mg, 0.49 mmol) were dissolved in 1,4-dioxane (20 mL). X-phos (48 mg, 0.1 mmol), cesium carbonate (473 mg, 1.5 mmol) and tris(dibenzylideneacetone)dipalladium(0) (46 mg, 0.05 mmol) were added. Under the protection of nitrogen gas, the resultant mixture was heated to 80° C. and reacted for 16 h. After suction filtration, the filtrate was concentrated, and subjected to silica gel column chromatography (petroleum ether:ethyl acetate=1:1) to obtain the product (160 mg, yield: 51%).

(8) Preparation of 5-chloro-$N^4$-(2-(isopropylsulfonyl)phenyl)-$N^2$-(6-methyl-7-(piperidin-4-yl)benzo[d][1,3]dioxol-4-yl)pyrimidine-2,4-diamine

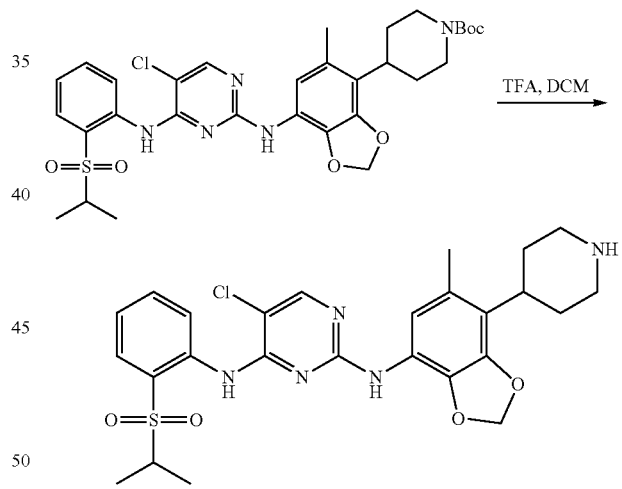

Tert-butyl 4-(7-((5-chloro-4-((2-(isopropylsulfonyl)phenyl)amino)pyrimidin-2-yl)amino)-5-methylbenzo[d][1,3]dioxol-4-yl)piperidin-1-carboxylate (160 mg, 0.25 mmol) was dissolved in dichloromethane (20 mL), and 10 mL trifluoroacetic acid was added. The resultant mixture was stirred at room temperature for 1 h. After the reaction, the resultant mixture was washed with sodium bicarbonate, dried with anhydrous sodium sulphate, filtrated, and concentrated to obtain the crude product. After silica gel column chromatography (dichloromethane:methanol=10:1), the final product was obtained (70 mg, yield: 52%).

Molecular formula: $C_{26}H_{30}ClN_5O_4S$ Molecular weight: 544.07 LC-MS (m/z): 544.2 $[M+H]^+$ $^1$H-NMR (400 MHz, MeOD) δ: 8.56 (d, J=8.0 Hz, 1H), 8.10 (s, 1H), 7.87 (dd, J=1.2 Hz, 8.0 Hz, 1H), 7.53-7.58 (m, 1H), 7.27-7.31 (m, 1H), 6.93 (s, 1H), 5.86 (s, 2H), 3.47-3.50 (m, 2H), 3.09-3.15 (m, 3H), 2.33-2.43 (m, 2H), 2.25 (s, 3H), 1.90-1.94 (m, 2H), 1.22-1.28 (m, 6H).

Example 2 Preparation of 2-((5-chloro-2-((6-methyl-7-(piperidin-4-yl)benzol[d][1,3]dioxol-4-yl)amino)pyrimidin-4-yl)amino)-N,N-dimethylbenzenesulfonamide (Compound 2)

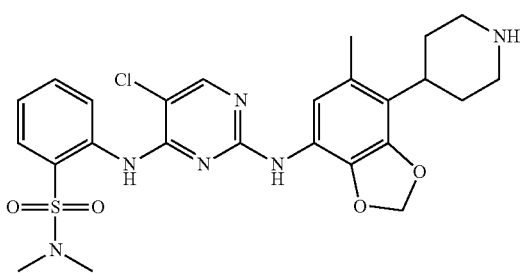 [SMILES: Cc1cc(Nc2ncc(Cl)c(Nc3ccccc3S(=O)(=O)N(C)C)n2)c2c(c1C1CCNCC1)OCO2]

(1) Preparation of N,N-dimethyl-2-nitrobenzenesulfonamide

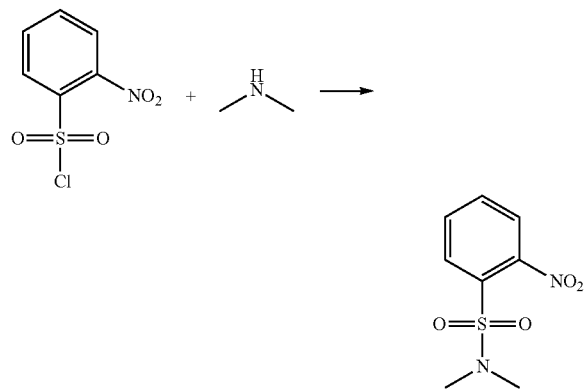

2-Nitrobenzenesulfonyl chloride (3 g, 13.5 mmol) was dissolved in 50 mL DMF, and dimethylamine (730 mg, 16.2 mmol) and K₂CO₃ (3.7 g, 26.8 mmol) were then added. The resultant mixture was reacted at 80° C. for 6 h. After the reaction, the resultant mixture was cooled to room temperature, and 100 mL water was added. After extraction with ethyl acetate (200 mL×2), the organic phases were combined, dried with anhydrous sodium sulphate, filtrated, and concentrated to obtain the product (2.8 g, yield: 90%).

(2) Preparation of 2-amino-N,N-dimethylbenzenesulfonamide

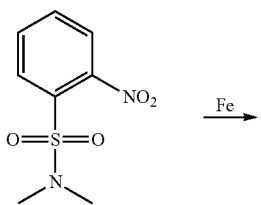

N,N-Dimethyl-2-nitrobenzenesulfonamide (2.8 g, 12.2 mmol) was dissolved in 50 mL EtOH/H₂O=4:1, andiron powder (3.4 g, 60.7 mmol) and NH₄Cl (64 mg, 1.2 mmol) were then added. The resultant mixture was stirred at 80° C. for 2 h. After the reaction, the resultant mixture was cooled to room temperature, and the insoluble substances were removed by filtration. The filtrate was extracted with ethyl acetate. The organic phase was washed with sodium bicarbonate solution and then aqueous NaCl solution, and dried with anhydrous sodium sulphate. The residue was subjected to column chromatography (petroleum ether:ethyl acetate=5:1) to obtain the product (2.0 g, yield: 82%).

(3) Preparation of 2-((2,5-dichloropyrimidin-4-yl)amino)-N,N-dimethylbenzenesulfonamide

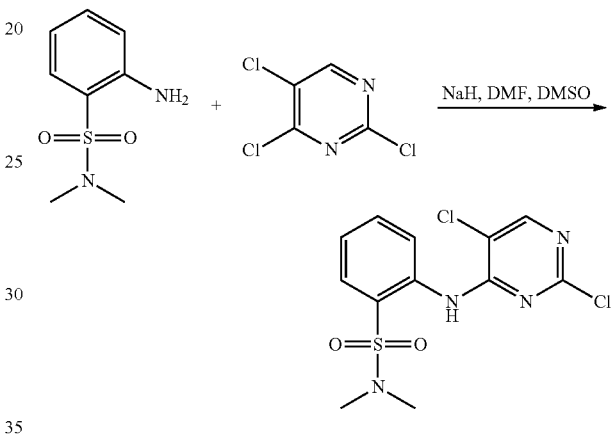

2-Amino-N,N-dimethylbenzenesulfonamide (2 g, 10 mmol) was dissolved in a mixed solvent of DMF (10 mL) and DMSO (1 mL). In ice batch, NaH (600 mg, 15 mmol, 60%) in a mixed solvent of DMF/DMSO (20/2 mL) was slowly added dropwise, and then 2,4,5-trichloropyrimidine (3.66 g, 20 mmol) in a mixed solvent of DMF/DMSO (10/1 mL) was slowly added dropwise. The resultant mixture was reacted at room temperature under stirring for 16 h. After the reaction, 100 mL water was added. After extraction with ethyl acetate (100 mL×2), the organic phases were combined, dried with anhydrous sodium sulphate, filtrated, and concentrated to obtain a crude product. After purification by silica gel column chromatography (petroleum ether:ethyl acetate=20:1), the product (1.6 g, yield: 46%) was obtained.

(4) Preparation of tert-butyl4-(7-((5-chloro-4-((2-(N,N-dimethylaminosulfonyl)phenyl)amino) pyrimidin-2-yl)amino)-5-methylbenzo[d][1,3]dioxol-4-yl)piperidin-1-carboxylate

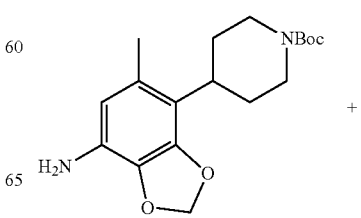

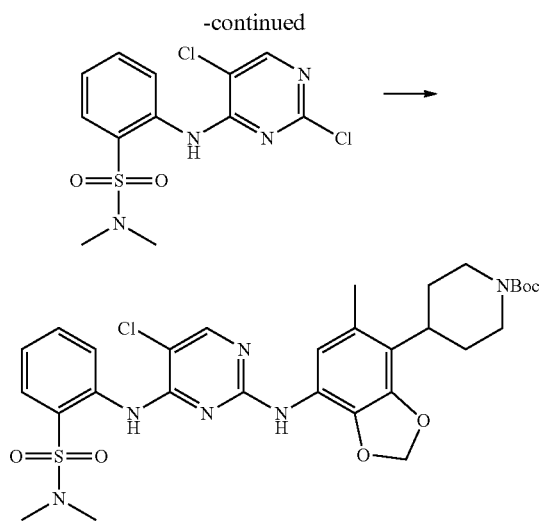

Tert-butyl4-(7-amino-5-methylbenzo[d][1,3]dioxol-4-yl)piperidin-1-carboxylate (prepared by the method described in Steps (1)-(6) of Example 1, 200 mg, 0.6 mmol) and 2-((2,5-dichloropyrimidin-4-yl)amino)-N,N-dimethylbenzenesulfonamide (173 mg, 0.5 mmol) were dissolved in 1,4-dioxane (20 mL). X-phos (48 mg, 0.1 mmol), cesium carbonate (585 mg, 1.8 mmol) and tris(dibenzylideneacetone)dipalladium(0) (46 mg, 0.05 mmol) were added. Under the protection of nitrogen gas, the resultant mixture was heated to 80° C. and reacted for 16 h. After suction filtration, the filtrate was concentrated, and subjected to silica gel column chromatography (petroleum ether:ethyl acetate=1:1) to obtain the product (90 mg, yield: 23%).

(5) Preparation of 2-((5-chloro-2-((6-methyl-7-(piperidin-4-yl)benzo[d][1,3]dioxol-4-yl)amino) pyrimidin-4-yl)amino)-N,N-dimethylbenzenesulfonamide

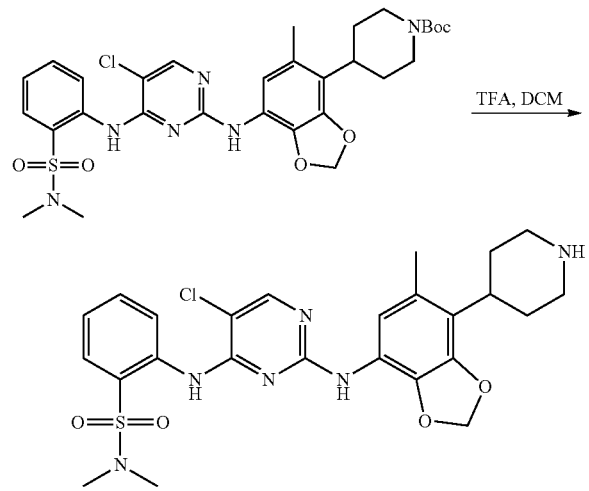

Tert-butyl4-(7-((5-chloro-4-((2-(N,N-dimethylaminosulfonyl)phenyl)amino)pyrimidin-2-yl) amino)-5-methylbenzo[d][1,3]dioxol-4-yl)piperidin-1-carboxylate (90 mg, 0.14 mmol) was dissolved in dichloromethane (10 mL), and 5 mL trifluoroacetic acid was added. The resultant mixture was stirred at room temperature for 1 h. After the reaction, the resultant mixture was washed with sodium bicarbonate solution, dried with anhydrous sodium sulphate, filtrated, and concentrated to obtain a crude product. After purified by silica gel column chromatography (dichloromethane:methanol=10:1), the final product (45 mg, yield: 59%) was obtained.

Molecular formula: $C_{25}H_{29}ClN_6O_4S$ Molecular weight: 545.06 LC-MS (m/z): 545.2 $[M+H]^+$ $^1$H-NMR (400 MHz, CDCl$_3$) δ: 9.44 (s, 1H), 8.54 (d, J=8.4 Hz, 1H), 8.13 (s, 1H), 7.87 (dd, J=1.2 Hz, 8.0 Hz, 1H), 7.52-7.55 (m, 1H), 7.36 (s, 1H), 7.21-7.25 (m, 1H), 6.79 (s, 1H), 5.94 (s, 2H), 3.58-3.61 (m, 2H), 2.88-3.01 (m, 3H), 2.74 (s, 6H), 2.52-2.58 (m, 2H), 2.21 (s, 3H), 1.81-1.88 (m, 2H).

Example 3 Preparation of 2-((5-chloro-2-((7-methyl-8-(piperidin-4-yl)-2,3-dihydrobenzo[b][1,4]dioxin-5-yl)amino)pyrimidin-4-yl)amino)-N,N-dimethylbenzenesulfonamide (Compound 3)

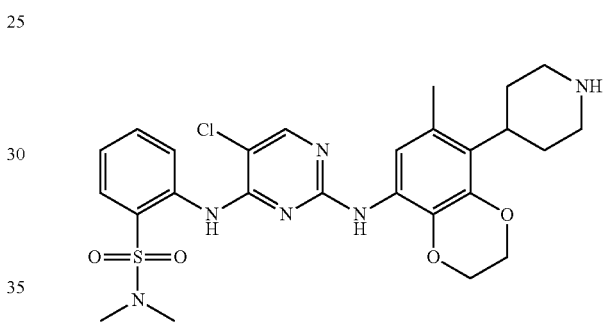

(1) Preparation of N,N-dimethyl-2-nitrobenzenesulfonamide

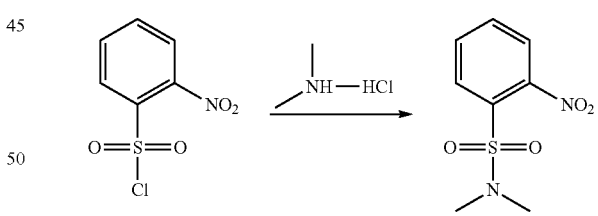

2-Nitrobenzenesulfonyl chloride (4.43 g, 20 mmol) was dissolved in dichloromethane (50 mL), and triethylamine (8.08 g, 80 mmol) and dimethylamine hydrochloride (1.63 g, 20 mmol) were added. The resultant mixture was reacted at room temperature for 12 h. Water (100 mL) was added. After extraction with ethyl acetate (150 mL×2), the organic phases were combined, washed with saturated NaCl aqueous solution, dried with anhydrous sodium sulphate, and concentrated in vacuum. The crude product was purified by silica gel column chromatography (petroleum ether:ethyl acetate=3:1) to obtain the product (2.53 g, yield: 55%).

(2) Preparation of 2-amino-N,N-dimethylbenzenesulfonamide

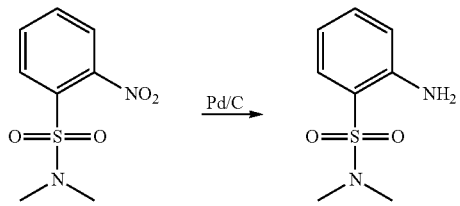

N,N-Dimethyl-2-nitrobenzenesulfonamide (2.5 g, 10.9 mmol) was dissolved in methanol (100 mL), and Pd/C (250 mg) was added. Hydrogen gas was introduced, and the resultant mixture was stirred at room temperature for 12 h. After the reaction, Pd/C was removed by filtration. The solvent was removed by rotary evaporation to obtain the product (2 g, yield: 92%).

(3) Preparation of 2-((2,5-dichloropyrimidin-4-yl)amino)-N,N-dimethylbenzenesulfonamide

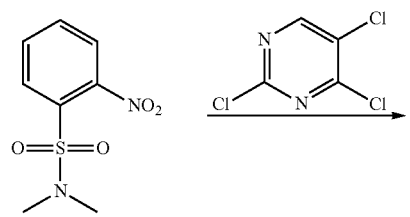

2-Amino-N,N-dimethylbenzenesulfonamide (2 g, 9.99 mmol) was dissolved in N,N-dimethyl formamide (50 mL), and sodium hydride (a mass fraction of 60%, 800 mg, 20 mmol) and 2,4,5-trichloropyrimidine (2.2 g, 12 mmol) were added. The resultant mixture was reacted at room temperature for 12 h. Water (100 mL) was added. After extraction with ethyl acetate (150 mL×2), the organic phases were combined, washed with saturated NaCl aqueous solution, dried with anhydrous sodium sulphate, and concentrated in vacuum. The crude product was purified by silica gel column chromatography (petroleum ether:ethyl acetate=3:1) to obtain the product (500 mg, yield: 14.4%).

(4) Preparation of tert-butyl 4-(8-((5-chloro-4-((2-(N,N-dimethylaminosulfonyl)phenyl)amino)pyrimidin-2-yl)amino)-6-methyl-2,3-dihydrobenzo[b][1,4]dioxin-5-yl)piperidin-1-carboxylate

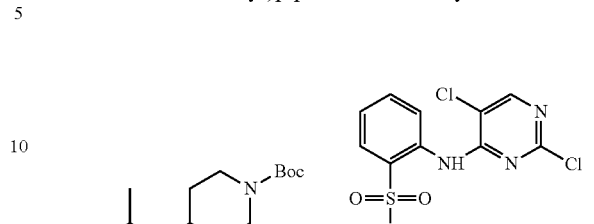

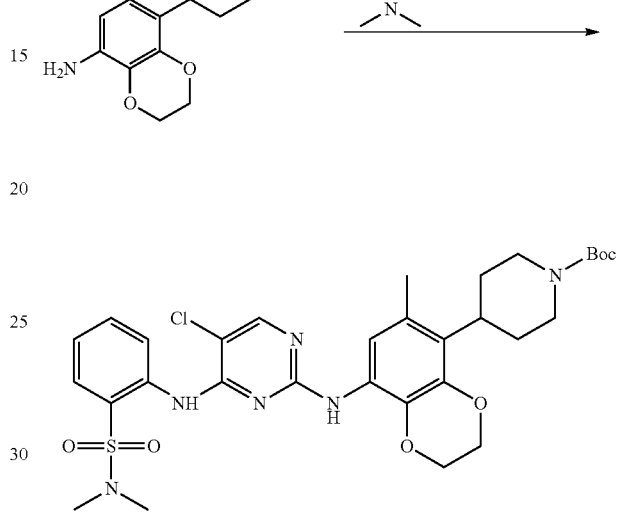

Tert-butyl 4-(8-amino-6-methyl-2,3-dihydrobenzo[b][1,4]dioxin-5-yl)piperidin-1-carboxylate (prepared by the method described in Steps (1)-(8) of Example 4, 348 mg, 1 mmol), 2-((2,5-dichloropyrimidin-4-yl)amino)-N,N-dimethylbenzenesulfonamide (347 mg, 1 mmol), tris(dibenzylideneacetone)dipalladium(0) (35 mg), 2-dicyclohexylphosphino-2',4',6'-triisopropylbiphenyl (70 mg) and cesium carbonate (977 mg, 3 mmol) were added to dioxane (10 mL). Under the protection of nitrogen gas, the resultant mixture was microwave-heated to 120° C. and reacted for 2 h. After cooling to room temperature, insoluble substances were removed by filtration. After concentration in vacuum, the crude product was purified by silica gel column chromatography (ethyl acetate:petroleum ether=1:2) to obtain the product (75 mg, yield: 11.4%).

(5) Preparation of 2-((5-chloro-2-((7-methyl-8-(piperidin-4-yl)-2,3-dihydrobenzo[b][1,4]dioxin-5-yl)amino)pyrimidin-4-yl)amino)-N,N-dimethylbenzenesulfonamide

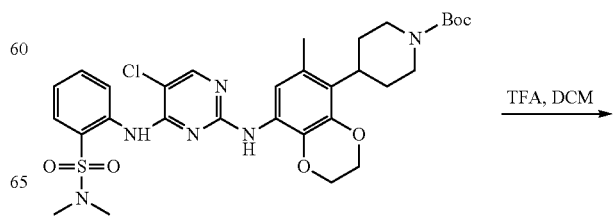

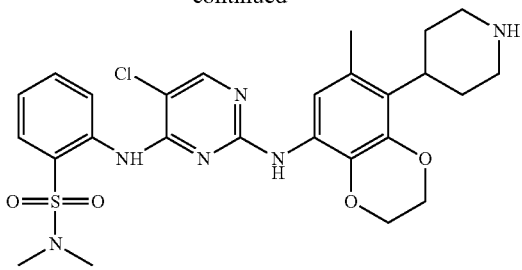

Tert-butyl 4-(8-((5-chloro-4-((2-(N,N-dimethylaminosulfonyl)phenyl)amino)pyrimidin-2-yl)amino)-6-methyl-2,3-dihydrobenzo[b][1,4]dioxin-5-yl)piperidin-1-carboxylate (75 mg, 0.114 mmol) was dissolved in dichloromethane (10 mL), and trifluoroacetic acid (1 mL) was added. After stirring at room temperature for 12 h, TLC detection showed that the raw materials disappeared. Water (20 mL) was added, and phases were separated. The water phase was extracted with dichloromethane (20 mL×2) twice. The organic phases were combined, and dried with anhydrous sodium sulphate. The solvent was removed by rotary evaporation, and the crude product was purified by silica gel column chromatography (methanol:dichloromethane=1:50) to obtain the final product (30 mg, yield: 47.2%).

Molecular formula: $C_{26}H_{31}ClN_6O_4S$ Molecular weight: 559.08 LC-MS (m/z): 280.2[M/2+H]$^+$ $^1$H-NMR (400 MHz, MeOD) δ: 8.44 (d, 1H, J=1.2), 8.11 (s, 1H), 7.86 (d, 1H, J=1.2), 7.56-7.60 (m, 1H), 7.28-7.35 (m, 2H), 4.26 (s, 4H), 3.45-3.48 (m, 2H), 3.06-3.15 (m, 3H), 2.56-2.74 (m, 8H), 2.17 (s, 3H), 1.76-1.80 (m, 2H).

Example 4 Preparation of 5-chloro-N$^4$-(2-(isopropylsulfonyl)phenyl)-N$^2$-(7-methyl-8-(piperidin-4-yl)-2,3-dihydrobenzo[b][1,4]dioxin-5-yl)pyrimidine-2,4-diamine (Compound 4)

(1) Preparation of 2-methoxy-4-methyl-6-nitrophenol

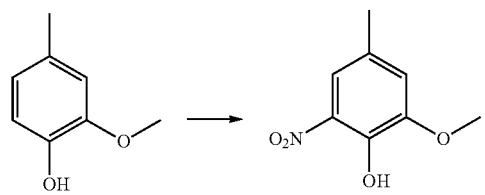

2-Methoxy-4-methylphenol (55 g, 398.1 mmol) was dissolved in trichloromethane (1000 mL). After cooling to −10° C., fuming nitric acid (25.1 g, 398.4 mmol) was dissolved in glacial acetic acid (100 mL), and added dropwise to the reaction bottle. After the addition, TLC detection showed that the raw materials disappeared. Water was added to quench the reaction, and phases were separated. The organic phase was washed with water, washed with saturated NaCl aqueous solution, dried with anhydrous sodium sulphate, concentrated in vacuum, and recrystallized from methanol to obtain the product (35 g, yield: 48%).

(2) Preparation of 5-methyl-3-nitrobenzene-1,2-diol

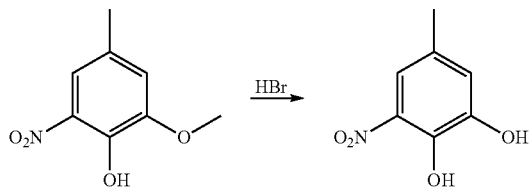

2-Methoxy-4-methyl-6-nitrophenol (35 g, 191.1 mmol) was dissolved in hydrobromic acid (500 mL), and tetrabutylammonium fluoride trihydrate (3.5 g, 11.1 mmol) was added. After reacting at 110° C. for 12 h, TLC detection showed that the raw materials were completely reacted. Insoluble substances were removed by filtration, and water (1 L) was added. After extraction with ethyl acetate (500 mL×2), the organic phases were combined, and dried with anhydrous sodium sulphate. The solvent was removed by rotary evaporation to obtain the product (23.3 g, yield: 72%).

(3) Preparation of 7-methyl-5-nitro-2,3-dihydrobenzo[b][1,4]dioxin

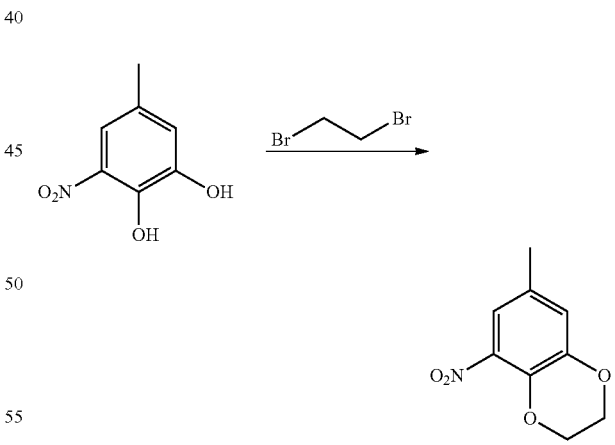

5-Methyl-3-nitrobenzene-1,2-diol (23.3 g, 137.8 mmol) was dissolved in N,N-dimethyl formamide (200 mL), and potassium carbonate (57.07 g, 413.6 mmol) and 1,2-dibromoethane (51.8 g, 275.7 mmol) were added. The resultant mixture was stirred at 55° C. for 12 h. After the reaction, insoluble substances were removed by filtration, and water was added (500 mL). After extraction with ethyl acetate (500 mL×2), the organic phases were combined, and dried with anhydrous sodium sulphate. The solvent was removed by rotary evaporation, and the crude product was purified by (4) Preparation of 6-bromo-7-methyl-5-nitro-2,3-dihydrobenzo[b][1,4]dioxin

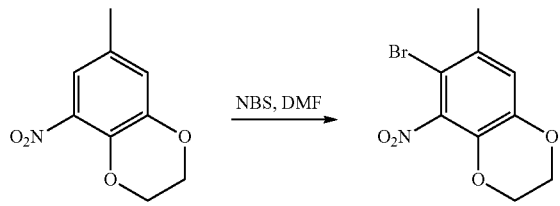

7-Methyl-5-nitro-2,3-dihydrobenzo[b][1,4]dioxin (20 g, 102.5 mmol) was dissolved in N,N-dimethyl formamide (250 mL), and N-bromosuccinimide (36.5 g, 205.1 mmol) was added. After reacting at 55° C. for 12 h, insoluble substances were removed by filtration, and water was added (500 mL). After extraction with ethyl acetate (250 mL×2), the organic phases were combined, washed with saturated NaCl aqueous solution, dried with anhydrous sodium sulphate, and concentrated in vacuum. The crude product was purified by silica gel column chromatography (petroleum ether:ethyl acetate=10:1) to obtain the product (17.5 g, yield: 62%).

(5) Preparation of 6-bromo-7-methyl-2,3-dihydrobenzo[b][1,4]dioxin-5-amine

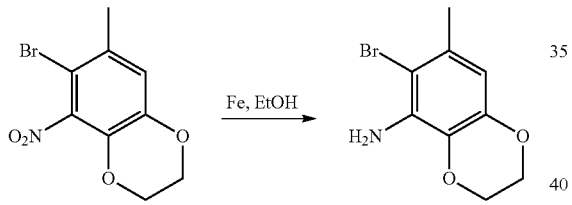

6-Bromo-7-methyl-5-nitro-2,3-dihydrobenzo[b][1,4]dioxin (17.5 g, 63.85 mmol) was dissolved in ethanol (500 mL), and iron powder (54 g, 964.3 mmol) and glacial acetic acid (100 mL) were added. After reacting at 80° C. for 2 h, insoluble substances were removed by filtration, and water (500 mL) was added. After extraction with ethyl acetate (250 mL×2), the organic phases were combined, washed with saturated NaCl aqueous solution, dried with anhydrous sodium sulphate, and concentrated in vacuum. The crude product was purified by silica gel column chromatography (petroleum ether:ethyl acetate=3:1) to obtain the product (10 g, yield: 64%).

(6) Preparation of 6-bromo-8-iodo-7-methyl-2,3-dihydrobenzo[b][1,4]dioxin-5-amine

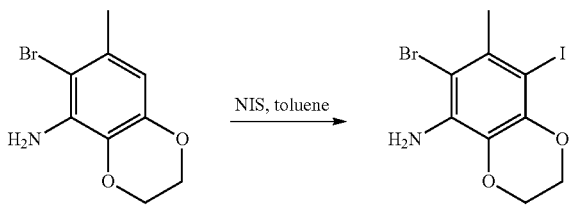

6-Bromo-7-methyl-2,3-dihydrobenzo[b][1,4]dioxin-5-amine (10 g, 40.97 mmol) was added to toluene (100 mL), and N-iodosuccinimide (14 g, 62.22 mmol) and glacial acetic acid (2.5 mL) were added. After reacting at room temperature for 2 h, insoluble substances were removed by filtration, and water (200 mL) was added. After extraction with ethyl acetate (150 mL×2), the organic phases were combined, washed with saturated NaCl aqueous solution, dried with anhydrous sodium sulphate, and concentrated in vacuum. The crude product was purified by silica gel column chromatography (petroleum ether:ethyl acetate=3:1) to obtain the product (8 g, yield: 53%).

(7) Preparation of tert-butyl 4-(8-amino-7-bromo-6-methyl-2,3-dihydrobenzo[b][1,4]dioxin-5-yl)-3,6-dihydropyridine-1(2H)-carboxylate

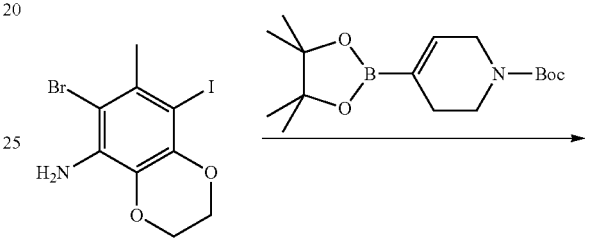

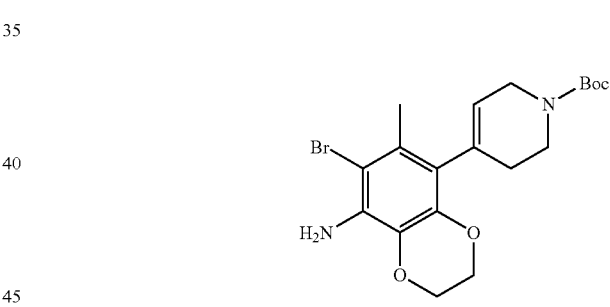

6-Bromo-8-iodo-7-methyl-2,3-dihydrobenzo[b][1,4]dioxin-5-amine (8 g, 21.62 mmol) was dissolved in dioxane (100 mL), and tert-butyl 4-(4,4,5,5-tetramethyl-1,3,2-dioxaborolan-2-yl)-3,6-dihydropyridine-1(2H)-carboxylate (6 g, 19.4 mmol), 1,1'-bis(diphenylphosphino)ferrocene-palladium(II)dichloride dichloromethane complex (800 mg) and potassium carbonate (8.03 g, 58.2 mmol) were added. Under the protection of nitrogen gas, the resultant mixture was reacted at 90° C. for 16 h. TLC detection showed that the raw materials were reacted completely, insoluble substances were removed by filtration, and water (200 mL) was added. After extraction with ethyl acetate (200 mL×2), the organic phases were combined, and dried with anhydrous sodium sulphate. The crude product was purified by silica gel column chromatography (petroleum ether:ethyl acetate=3:1) to obtain the product (4.5 g, yield: 55%).

(8) Preparation of tert-butyl 4-(8-amino-6-methyl-2,3-dihydrobenzo[b][1,4]dioxin-5-yl)piperidin-1-carboxylate

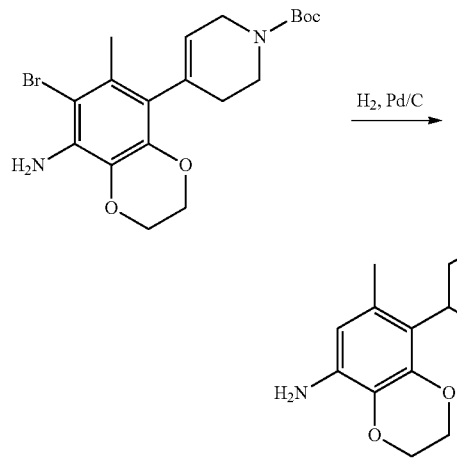

Tert-butyl 4-(8-amino-7-bromo-6-methyl-2,3-dihydrobenzo[b][1,4]dioxin-5-yl)-3,6-dihydropyridine-1(2H)-carboxylate (4.5 g, 10.58 mmol) was dissolved in methanol (200 mL), and Pd/C (4.5 g) was added. The resultant mixture was stirred at room temperature for 12 h. After the reaction, Pd/C was removed by filtration, and the solvent was removed by rotary evaporation to obtain the product (1.5 g, yield: 41%).

(9) Preparation of 2,5-dichloro-N-(2-(isopropylsulfonyl)phenyl)pyrimidin-4-amine

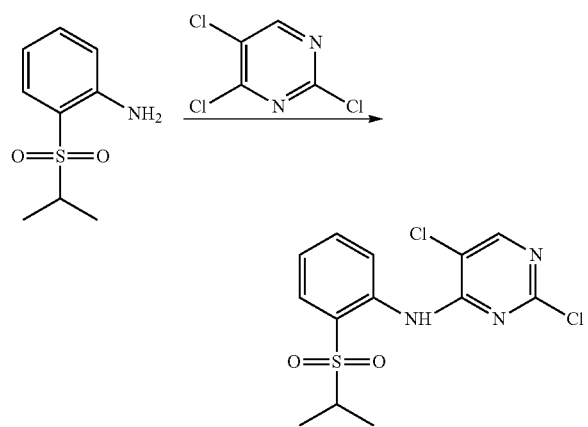

2-(Isopropylsulfonyl)aniline (1.99 g, 10 mmol) and 2,4,5-trichloropyrimidine (2.2 g, 11.99 mmol) were dissolved in N,N-dimethyl formamide (30 mL), and sodium hydride (a mass fraction of 60%, 0.8 g, 20 mmol) was added. After reacting at room temperature for 12 h, water was added (100 mL). After extraction with ethyl acetate (150 mL×2), the organic phases were combined, washed with saturated NaCl aqueous solution, dried with anhydrous sodium sulphate, and concentrated in vacuum. The crude product was purified by silica gel column chromatography (petroleum ether:ethyl acetate=25:1) to obtain the product (1.59 g, yield: 46%).

(10) Preparation of tert-butyl4-(8-((5-chloro-4-((2-(isopropylsulfonyl)phenyl)amino)pyrimidin-2-yl)amino)-6-methyl-2,3-dihydrobenzo[b][1,4]dioxin-5-yl)piperidin-1-carboxylate

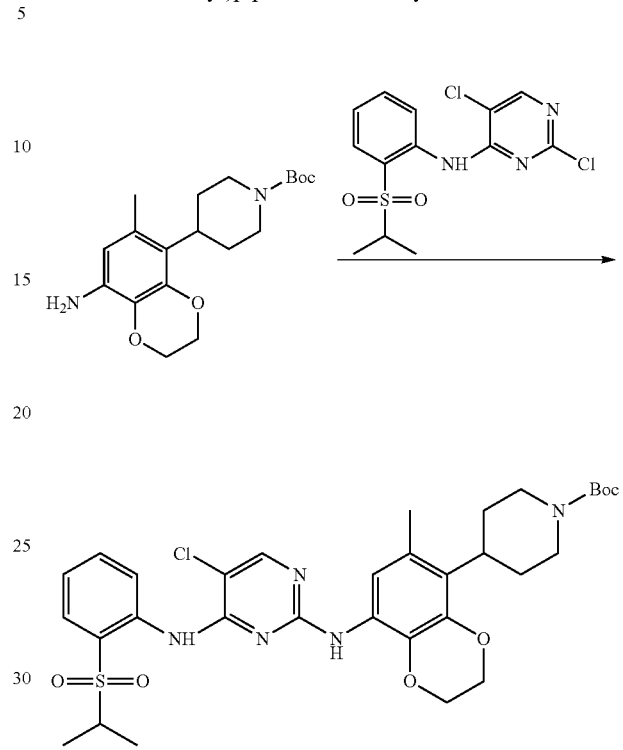

Tert-butyl4-(8-amino-6-methyl-2,3-dihydrobenzo[b][1,4]dioxin-5-yl)piperidin-1-carboxylate (348 mg, 1 mmol), 2,5-dichloro-N-(2-(isopropylsulfonyl)phenyl)pyrimidin-4-amine (346 mg, 1 mmol), tris(dibenzylideneacetone)dipalladium(0) (35 mg), 2-dicyclohexylphosphino-2',4',6'-triisopropylbiphenyl (70 mg) and cesium carbonate (977 mg, 3 mmol) were added to dioxane (10 mL). Under the protection of nitrogen gas, the resultant mixture was heated to 90° C. and reacted for 12 h. After cooling to room temperature, insoluble substances were removed by filtration. After concentration in vacuum, the crude product was purified by silica gel column chromatography (ethyl acetate:petroleum ether=1:2) to obtain the product (90 mg, yield: 13.7%).

(11) Preparation of 5-chloro-$N^4$-(2-(isopropylsulfonyl)phenyl)-$N^2$-(7-methyl-8-(piperidin-4-yl)-2,3-dihydrobenzo[b][1,4]dioxin-5-yl)pyrimidine-2,4-diamine

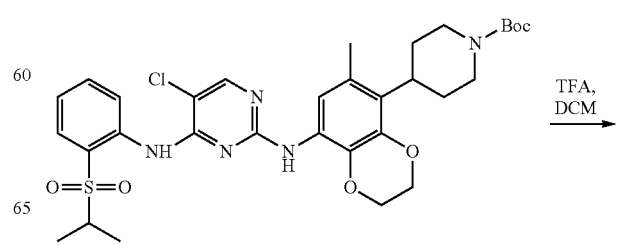

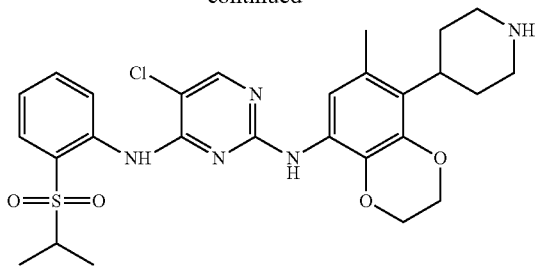

Tert-butyl4-(8-((5-chloro-4-((2-(isopropylsulfonyl)phenyl)amino)pyrimidin-2-yl)amino)-6-methyl-2,3-dihydrobenzo[b][1,4]dioxin-5-yl)piperidin-1-carboxylate (90 mg, 0.137 mmol) was dissolved in dichloromethane (10 mL), and trifluoroacetic acid (1 mL) was added. After stirring at room temperature for 12 h, TLC detection showed that the raw materials disappeared. Water (10 mL) was added, and phases were separated. The water phase was extracted with dichloromethane (10 mL×2). The organic phases were combined, and dried with anhydrous sodium sulphate. The solvent was removed by rotary evaporation. The crude product was purified by silica gel column chromatography (methanol:dichloromethane=1:50) to obtain the final product (50 mg, yield: 65.5%).

Molecular formula: $C_{27}H_{32}ClN_5O_4S$ Molecular weight: 558.09 LC-MS (m/z): 279.7[M/2+H]$^+$ $^1$H-NMR (400 MHz, MeOD) δ: 8.49 (d, 1H, J=1.2), 8.14 (s, 1H), 7.91 (dd, 1H, J1=1.2, J2=8.0), 7.63-7.67 (m, 1H), 7.33-7.37 (m, 2H), 4.27 (s, 4H), 3.45-3.48 (m, 2H), 3.06-3.17 (m, 3H), 2.57-2.67 (m, 2H), 2.18 (s, 3H), 1.78-1.81 (m, 2H), 1.25-1.29 (m, 6H).

Example 5 Preparation of 5-chloro-N$^4$-(2-(isopropylsulfonyl)phenyl)-N$^2$-(7-methyl-8-(pyrrolidin-3-yl)-2,3-dihydrobenzo[b][1,4]dioxin-5-yl)pyrimidine-2,4-diamine (Compound 5)

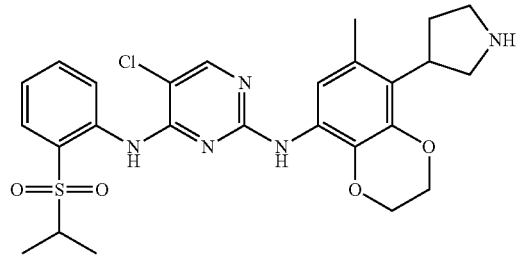 [SMILES: Cc1cc(Nc2ncc(Cl)c(Nc3ccccc3S(=O)(=O)C(C)C)n2)c2c(c1C1CCNC1)OCCO2]

(1) Preparation of 2-methoxy-4-methyl-6-nitrophenol

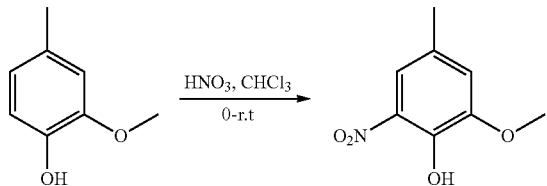

2-Methoxy-4-methylphenol (60 g, 434 mmol) was dissolved in chloroform (500 mL). At 0° C., to the system, acetic acid (150 mL) was added, and then fuming nitric acid (27.4 g, 435 mmol) was added dropwise. After the reaction, the solvent was evaporated to dryness, and the residue was recrystallized from methanol to obtain the product (29 g, yield: 36%).

(2) Preparation of 5-methyl-3-nitrobenzene-1,2-diol

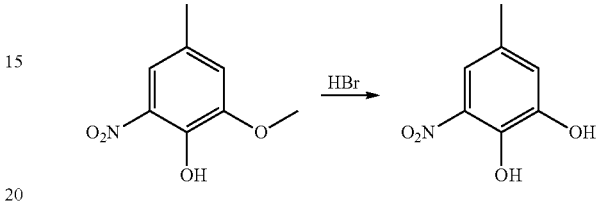

2-Methoxy-4-methyl-6-nitrophenol (29 g, 158 mmol) was dissolved in HBr (40%, 500 mL), and tetrabutylammonium fluoride (41 g, 157 mmol) was added. The resultant mixture was reacted at 110° C. under stirring for 4 h. After the reaction, the resultant mixture was cooled to room temperature, and 500 mL water was added. After extraction with ethyl acetate (200 mL×3), the organic phases were combined, washed with saturated NaCl aqueous solution (300 mL), dried with anhydrous sodium sulphate, and filtrated. The filtrate was concentrated to obtain the product (19.5 g, yield: 73%).

(3) Preparation of 7-methyl-5-nitro-2,3-dihydrobenzo[b][1,4]dioxin

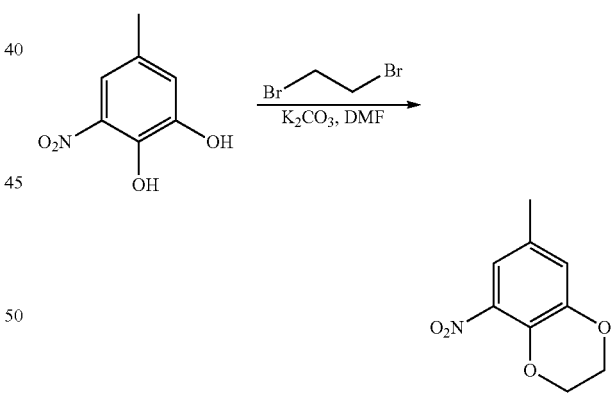

5-Methyl-3-nitrobenzene-1,2-diol (9.5 g, 56.2 mmol) was dissolved in DMF (200 mL), and 1,2-dibromoethane (21 g, 112 mmol) and potassium carbonate (23 g, 167 mmol) were added. The resultant mixture was heated to 55° C. and reacted under stirring for 16 h. After the reaction, the resultant mixture was cooled to room temperature, and 300 mL water was added. After extraction with ethyl acetate (200 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=30:1) to obtain the product (8.5 g, yield: 78%).

(4) Preparation of 6-bromo-7-methyl-5-nitro-2,3-dihydrobenzo[b][1,4]dioxin

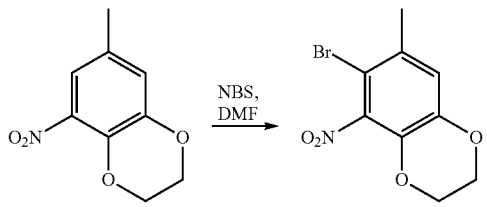

7-Methyl-5-nitro-2,3-dihydrobenzo[b][1,4]dioxin (8.5 g, 43.6 mmol) was dissolved in DMF (150 mL), and NBS (15.5 g, 87.1 mmol) was added. The resultant mixture was heated to 55° C. and reacted under stirring for 16 h. After the reaction, the resultant mixture was cooled to room temperature, and 300 mL water was added. After extraction with ethyl acetate (200 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=30:1) to obtain the product (7.3 g, yield: 61%).

(5) Preparation of 6-bromo-7-methyl-2,3-dihydrobenzo[b][1,4]dioxin-5-amine

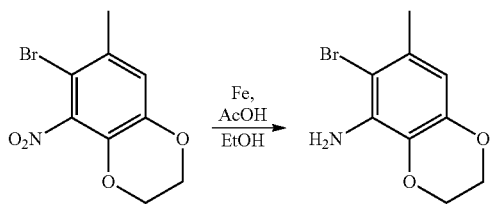

6-Bromo-7-methyl-5-nitro-2,3-dihydrobenzo[b][1,4]dioxin (7.3 g, 26.6 mmol) was dissolved in ethanol (150 mL), and acetic acid (30 mL) and iron powder (7.4 g, 132 mmol) were added. The resultant mixture was heated to 80° C. and reacted under stirring for 16 h. After the reaction, the resultant mixture was cooled to room temperature, and filtrated. To the filtrate, 200 mL water was added. After extraction with ethyl acetate (200 mL×3), the organic phases were combined, washed with saturated NaCl aqueous solution, dried with anhydrous sodium sulphate, filtrated, and concentrated. The crude product was purified by silica gel column chromatography (petroleum ether:ethyl acetate=20:1) to obtain the product (4.5 g, yield: 69%).

(6) Preparation of 6-bromo-8-iodo-7-methyl-2,3-dihydrobenzo[b][1,4]dioxin-5-amine

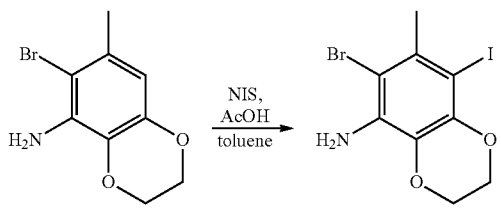

6-Bromo-7-methyl-2,3-dihydrobenzo[b][1,4]dioxin-5-amine (4.5 g, 18.4 mmol) was dissolved in toluene (40 mL), and NIS (6.2 g, 27.6 mmol) and acetic acid (1.5 mL) were added. The resultant mixture was reacted at room temperature under stirring for 2 h. After the reaction, 50 mL ice water was added, and the resultant mixture was extracted with ethyl acetate (100 mL×3). The organic phases were combined, washed with saturated NaCl aqueous solution, dried with anhydrous sodium sulphate, filtrated, and concentrated. The crude product was purified by silica gel column chromatography (petroleum ether:ethyl acetate=20:1) to obtain the product (4.0 g, yield: 59%).

(7) Preparation of tert-butyl 3-(((trifluoromethyl)sulfonyl)oxy)-2,5-dihydro-1H-pyrrole-1-carboxylate

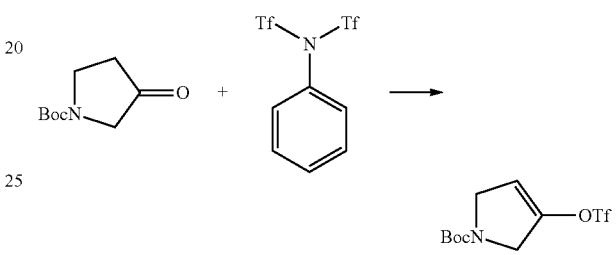

Tert-butyl 3-oxopyrrolidin-1-carboxylate (5.0 g, 27 mmol) was dissolved in tetrahydrofuran (50 mL). At −78° C., to the system, lithium diisopropylamide (20 mL, 40 mmol, 2 M) was slowly added dropwise, and after stirring for 10 min, a solution of 1,1,1-trifluoro-N-phenyl-N-((trifluoromethyl)sulfonyl)methylsulfonamide (11.6 g, 32.5 mmol) in tetrahydrofuran (50 mL) was added. After stirring for 30 min, the resultant mixture was placed at room temperature and reacted for 2 h. After the reaction, the resultant mixture was concentrated to obtain a crude product, which was directly used in the next step without purification.

(8) Preparation of tert-butyl 3-(4,4,5,5-tetramethyl-1,3,2-dioxaborolan-2-yl)-2,5-dihydro-1H-pyrrole-1-carboxylate

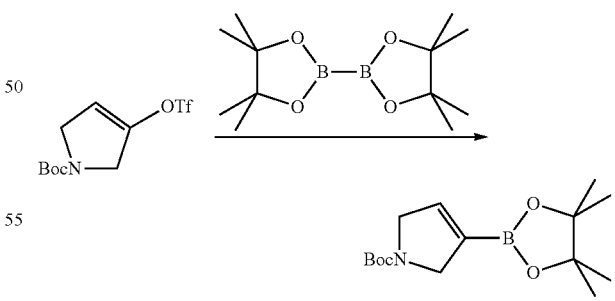

The crude product of tert-butyl 3-(((trifluoromethyl)sulfonyl)oxy)-2,5-dihydro-1H-pyrrole-1-carboxylate, bis(pinacolato)diboron (3.8 g, 15.0 mmol), potassium acetate (3.7 g, 37.7 mmol), 1,1'-bis (diphenylphosphino)ferrocene-palladium(II) dichloride dichloromethane complex (308 mg, 0.4 mmol) and 1,1'-bis(diphenylphosphino)ferrocene (210 mg, 0.4 mmol) were dissolved in 1,4-dioxane (50 mL). Under the protection of nitrogen gas, the resultant mixture was reacted at 80° C. under stirring for 16 h. After the reaction, the resultant mixture was cooled to room temperature, and 100 mL water was added. After extraction with ethyl acetate (100 mL×2), the organic phases were combined, dried with anhydrous sodium sulphate, filtrated, and concentrated to obtain a crude product, which was directly used in the next step without purification.

(9) Preparation of tert-butyl 3-(8-amino-7-bromo-6-methyl-2,3-dihydrobenzo[b][1,4]dioxin-5-yl)-2,5-dihydro-1H-pyrrole-1-carboxylate

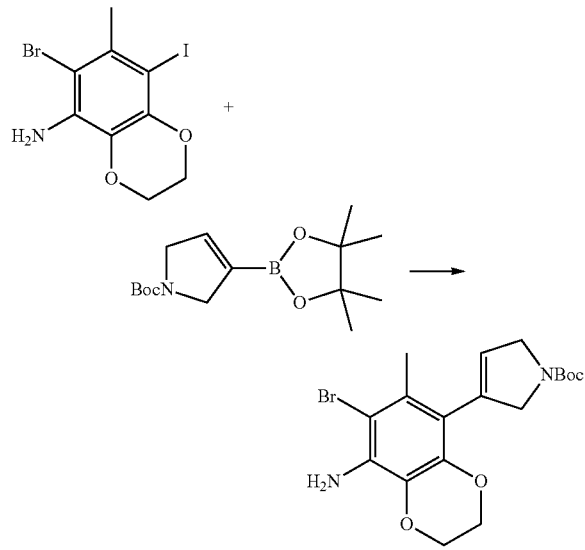

The crude product of tert-butyl3-(4,4,5,5-tetramethyl-1,3,2-dioxaborolan-2-yl)-2,5-dihydro-1H-pyrrole-1-carboxylate, and 6-bromo-8-iodo-7-methyl-2,3-dihydrobenzo[b][1,4]dioxin-5-amine (4.0 g, 10.8 mmol) were dissolved in a mixed solvent of 1,4-dioxane (50 mL) and water (20 mL). To the system, potassium carbonate (4.46 g, 32.3 mmol) and 1,1'-bis(diphenylphosphino)ferrocene-palladium(II) dichloride dichloromethane complex (444 mg, 0.54 mmol) were added. Under the protection of nitrogen gas, the resultant mixture was reacted at 80° C. under stirring for 2 h. After the reaction, the resultant mixture was cooled to room temperature, and 100 mL water was added. After extraction with ethyl acetate (100 mL×2), the organic phases were combined, dried with anhydrous sodium sulphate, filtrated, and concentrated to obtain a crude product. After purification by silica gel column chromatography (petroleum ether:ethyl acetate=10:1), the product (200 mg) was obtained.

(10) Preparation of tert-butyl 3-(8-amino-6-methyl-2,3-dihydrobenzo[b][1,4]dioxin-5-yl)pyrrolidin-1-carboxylate

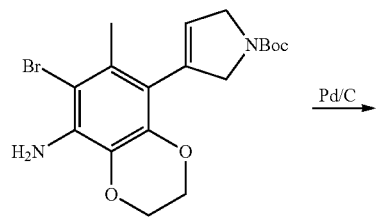

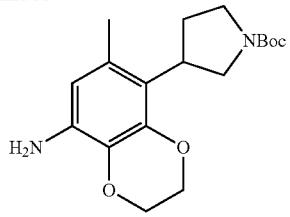

Tert-butyl3-(8-amino-7-bromo-6-methyl-2,3-dihydrobenzo[b][1,4]dioxin-5-yl)-2,5-dihydro-1H-pyrrole-1-carboxylate (200 mg, 0.49 mmol) was dissolved in methanol (20 mL). Under the protection of nitrogen gas, to the system, Pd/C (200 mg) was added, and then the system was reacted at the atmosphere of hydrogen gas at room temperature under stirring for 16 h. After the reaction, the resultant mixture was filtrated to prepare the product (100 mg, yield: 61%).

(11) Preparation of 2,5-dichloro-N-(2-(isopropylsulfonyl)phenyl)pyrimidin-4-amine

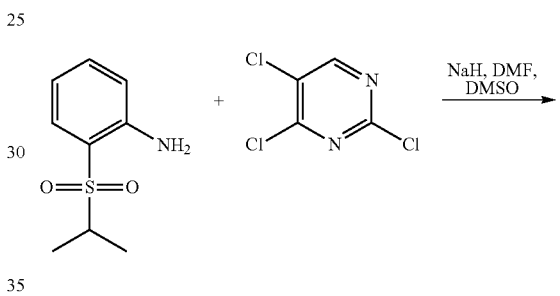

2-(Isopropylsulfonyl)aniline (2 g, 10 mmol) was dissolved in a mixed solvent of DMF (10 mL) and DMSO (1 mL). In ice bath, NaH (600 mg, 15 mmol, 60%) in a mixed solvent of DMF/DMSO (20/2 mL) was slowly added dropwise, and then 2,4,5-trichloropyrimidine (3.66 g, 20 mmol) in a mixed solvent of DMF/DMSO (10/1 mL) was slowly added dropwise. The resultant mixture was reacted at room temperature under stirring for 16 h. After the reaction, 100 mL water was added. After extraction with ethyl acetate (100 mL×2), the organic phases were combined, dried with anhydrous sodium sulphate, filtrated, and concentrated to obtain a crude product. After purification by silica gel column chromatography (petroleum ether:ethyl acetate=20:1), the product (1.8 g, yield: 52%) was obtained.

(12) Preparation of tert-butyl 3-(8-((5-chloro-4-((2-(isopropylsulfonyl)phenyl)amino)pyrimidin-2-yl)amino)-6-methyl-2,3-dihydrobenzo[b][1,4]dioxin-5-yl)pyrrolidin-1-carboxylate

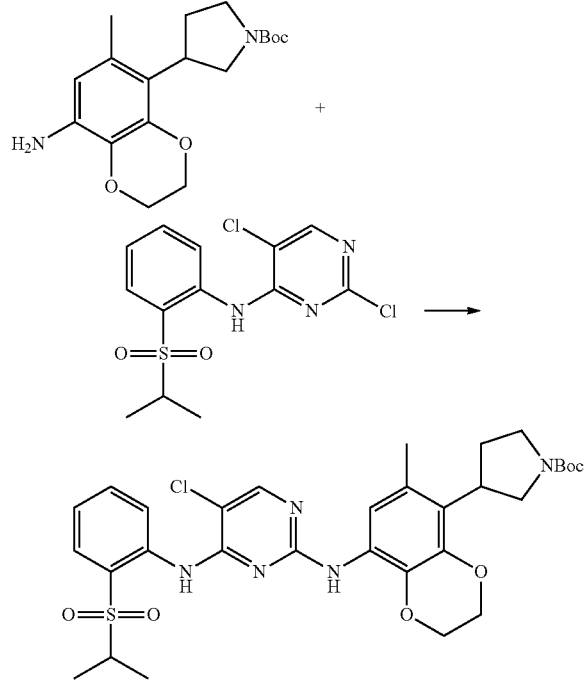

Tert-butyl3-(8-amino-6-methyl-2,3-dihydrobenzo[b][1,4]dioxin-5-yl)pyrrolidin-1-carboxylate (100 mg, 0.3 mmol) and 2,5-dichloro-N-(2-(isopropylsulfonyl)phenyl)pyrimidin-4-amine (124 mg, 0.36 mmol) were dissolved in 1,4-dioxane (20 mL). X-phos (29 mg, 0.06 mmol), cesium carbonate (293 mg, 0.9 mmol) and tris(dibenzylideneacetone)dipalladium(0) (28 mg, 0.03 mmol) were added. Under the protection of nitrogen gas, the resultant mixture was heated to 80° C. and reacted for 16 h. After suction filtration, the filtrate was concentrated, and the residue was subjected to silica gel column chromatography (petroleum ether:ethyl acetate=1:1) to obtain the product (50 mg, yield: 26%).

(13) Preparation of 5-chloro-$N^4$-(2-(isopropylsulfonyl)phenyl)-$N^2$-(7-methyl-8-(pyrrolidin-3-yl)-2,3-dihydrobenzo[b][1,4]dioxin-5-yl)pyrimidine-2,4-diamine

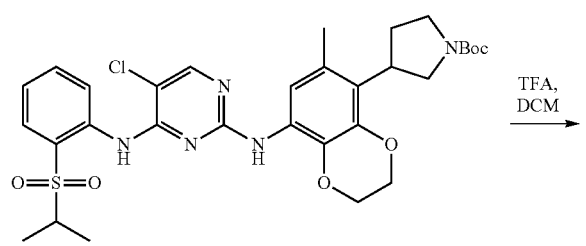

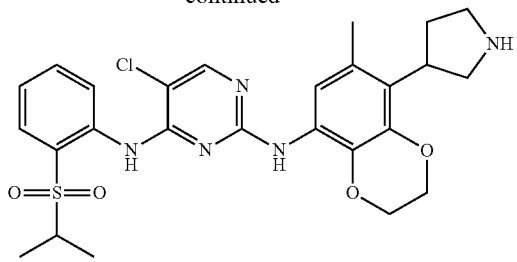

Tert-butyl 3-(8-((5-chloro-4-((2-(isopropylsulfonyl)phenyl)amino)pyrimidin-2-yl)amino)-6-methyl-2,3-dihydrobenzo[b][1,4]dioxin-5-yl)pyrrolidin-1-carboxylate (50 mg, 0.08 mmol) was dissolved in dichloromethane (10 mL), and 5 mL trifluoroacetic acid was added. The resultant mixture was stirred at room temperature for 1h. After the reaction, the resultant mixture was washed with sodium bicarbonate solution, dried with anhydrous sodium sulphate, filtrated, and concentrated to obtain a crude product. After silica gel column chromatography (dichloromethane:methanol=10:1), the final product (16 mg, yield: 38%) was obtained.

Molecular formula: $C_{26}H_{30}ClN_5O_4S$ Molecular weight: 544.07 LC-MS (m/z): 544.2 $[M+H]^+$ $^1$H-NMR (400 MHz, CDCl$_3$) δ: 9.55 (s, 1H), 8.56 (d, J=8.0 Hz, 1H), 8.16 (s, 1H), 7.93 (dd, J=1.6 Hz, 8.0 Hz, 1H), 7.61-7.67 (m, 2H), 7.33 (s, 1H), 7.25-7.29 (m, 1H), 4.42-4.53 (m, 2H), 4.31 (t, J=4.0 Hz, 2H), 3.65-3.78 (m, 3H), 3.48-3.53 (m, 1H), 3.33-3.36 (m, 1H), 3.23-3.27 (m, 1H), 2.32-2.35 (m, 1H), 2.22-2.28 (m, 1H), 2.19 (s, 3H), 1.22-1.32 (m, 6H).

Example 6 Preparation of $N^2$-(8-(azetidin-3-yl)-7-methyl-2,3-dihydrobenzo[b][1,4]dioxin-5-yl)-5-chloro-$N^4$-(2-(isopropylsulfonyl)phenyl)pyrimidine-2,4-diamine (Compound 6)

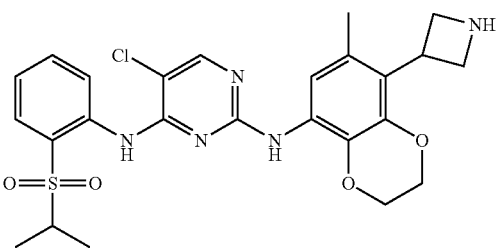 [SMILES: Cc1cc(Nc2ncc(Cl)c(Nc3ccccc3S(=O)(=O)C(C)C)n2)c2c(c1C1CNC1)OCCO2]

(1) Preparation of tert-butyl 3-((methylsulfonyl)oxy)azetidin-1-carboxylate

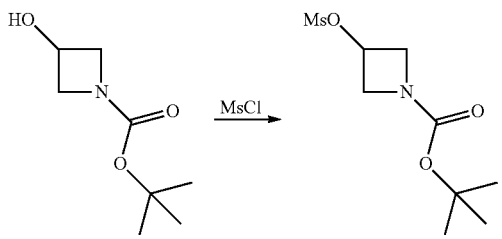 [SMILES: "MsCl" ; CC(C)(C)OC(=O)N1CC(O)C1 ; CC(C)(C)OC(=O)N1CC(OS(C)(=O)=O)C1]

Tert-butyl 3-hydroxyazetidin-1-carboxylate (2.0 g, 11.5 mmol) was dissolved in 50 mL tetrahydrofuran, and triethylamine (2.34 g, 23.1 mmol) was added. Under the condition of ice water bath, methanesulfonyl chloride (1.58 g, 13.8 mmol) was added slowly. The resultant mixture was warmed to room temperature, and further reacted for 4 h. After the reaction, the solvent was removed by rotary evaporation, and to the residue, 50 mL water was added. After extraction with ethyl acetate (3×50 mL), the organic phases were combined, dried with anhydrous sodium sulphate, and filtrated. The solvent was removed by rotary evaporation to obtain the product (2.67 g, yield: 92%).

(2) Preparation of tert-butyl 3-iodoazetidin-1-carboxylate

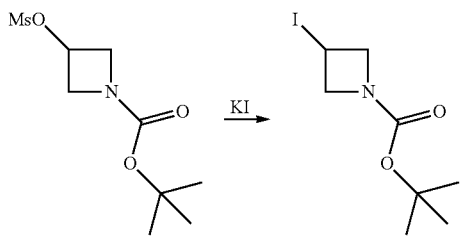

Tert-butyl 3-((methylsulfonyl)oxy)azetidin-1-carboxylate (2.67 g, 10.62 mmol) was dissolved in 20 mL N,N-dimethyl formamide, and potassium iodide (5.3 g, 31.93 mmol) was added. The resultant mixture was heated toil 0° C. and reacted for 16 h. After the reaction, the solvent was removed by rotary evaporation, and 50 mL water was added. After extraction with ethyl acetate (3×30 mL), the organic phases were combined, dried with anhydrous sodium sulphate, and filtrated. The solvent was removed by rotary evaporation, and the residue was subjected to silica gel column chromatography (petroleum ether:ethyl acetate=4:1) to obtain the product (2.5 g, yield: 83%).

(3) Preparation of 2-methoxy-4-methyl-6-nitrophenol

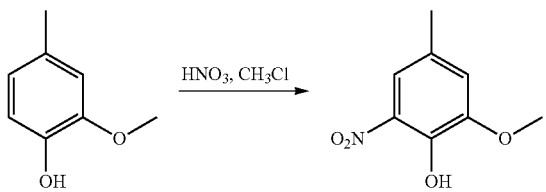

2-Methoxy-4-methylphenol (30.0 g, 0.217 mol) was dissolved in 0.8 L chloroform. After cooling to 0° C., fuming nitric acid (13.7 g, 0.217 mol) was dissolved in 70 mL acetic acid, and slowly added dropwise to the solution, during which the internal temperature was controlled below 0° C. The resultant mixture was warmed to room temperature and further reacted for 0.5 h. After complete reaction, the solvent was removed by rotary evaporation, 150 mL methanol was added to the residue. After filtration and drying in vacuum, the product (20 g, yield: 50%) was obtained.

(4) Preparation of 5-methyl-3-nitrobenzene-1,2-diol

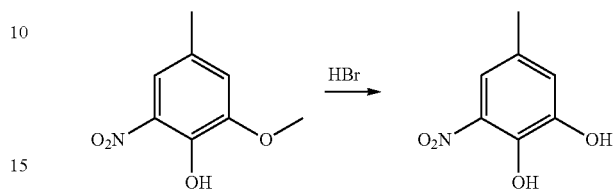

2-Methoxy-4-methyl-6-nitrophenol (20.0 g, 0.109 mol) was added to 150 mL hydrobromic acid (80%), and 15 g tetrabutylammonium fluoride was added. The resultant mixture was heated toll 0° C. and reacted for 18 h. After the reaction, 800 mL water was added. After extraction with ethyl acetate (5×400 mL), the organic phases were combined, washed with saturated NaCl aqueous solution (250 mL), dried with anhydrous sodium sulphate, and filtrated. The solvent was removed by rotary evaporation, and the residue was subjected to silica gel column chromatography (petroleum ether:ethyl acetate=5:1) to obtain the product (15 g, yield: 81%).

(5) Preparation of 7-methyl-5-nitro-2,3-dihydrobenzo[b][1,4]dioxin

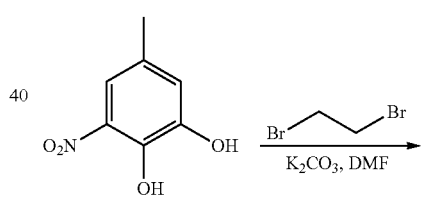

5-Methyl-3-nitrobenzene-1,2-diol (15 g, 88.7 mmol) was dissolved in 80 mL N,N-dimethyl formamide, and 1,2-dibromoethane (33.4 g, 177.8 mmol) and potassium carbonate (36.7 g, 265.6 mmol) were added. The resultant mixture was heated to 60° C., and the reaction was carried out overnight. After the reaction, 200 mL water was added, and the resultant mixture was extracted with ethyl acetate (3×100 mL). The organic phases were combined, the solvent was removed by rotary evaporation, and the residue was subjected to silica gel column chromatography (petroleum ether:ethyl acetate=5:1) to obtain the product (13 g, yield: 75%).

(6) Preparation of 6-bromo-7-methyl-5-nitro-2,3-dihydrobenzo[b][1,4]dioxin

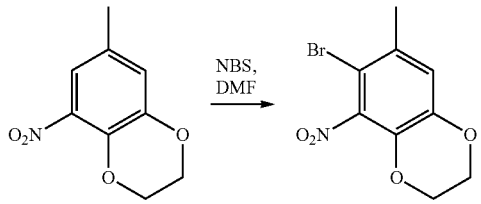

7-Methyl-5-nitro-2,3-dihydrobenzo[b][1,4]dioxin (13 g, 66.61 mmol) was dissolved in 200 mL N,N-dimethyl formamide, and N-bromosuccinimide (23.7 g, 133.2 mmol) was added in batch. The resultant mixture was heated to 60° C., and the reaction was carried out overnight. After the reaction, 200 mL water was added, and the resultant mixture was extracted with ethyl acetate (3×200 mL). The organic phases were combined, the solvent was removed by rotary evaporation, and the residue was subjected to silica gel column chromatography (petroleum ether:ethyl acetate=5:1) to obtain the product (12 g, yield: 66%).

(7) Preparation of 6-bromo-7-methyl-2,3-dihydrobenzo[b][1,4]dioxin-5-amine

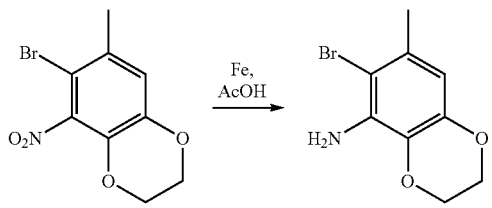

6-Bromo-7-methyl-5-nitro-2,3-dihydrobenzo[b][1,4]dioxin (12 g, 43.78 mmol) was dissolved in 160 mL ethanol, and 20 mL acetic acid was added. After heating to 70° C., iron powder (24.5 g, 437.5 mmol) was added in batch. After heating to 80° C., the reaction was carried out for 3 h. After the reaction, the resultant mixture was cooled to room temperature, and filtrated. To the filtrate, 300 mL water was added. The resultant mixture was extracted with ethyl acetate (3×300 mL). The organic phases were combined, the solvent was removed by rotary evaporation, and the residue was subjected to silica gel column chromatography (petroleum ether:ethyl acetate=2:1) to obtain the product (8 g, yield: 75%).

(8) Preparation of 6-bromo-8-iodo-7-methyl-2,3-dihydrobenzo[b][1,4]dioxin-5-amine

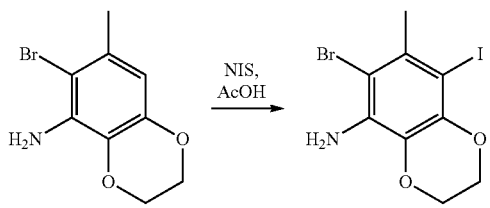

6-Bromo-7-methyl-2,3-dihydrobenzo[b][1,4]dioxin-5-amine (8 g, 32.77 mmol) was dissolved in 100 mL toluene, and 5 mL acetic acid and N-iodosuccinimide (11.1 g, 49.34 mmol) were added. The reaction was carried out at room temperature for 3 h. After the reaction, 100 mL water was added, and the resultant mixture was extracted with ethyl acetate (3×200 mL). The organic phases were combined, and washed with 200 mL sodium bisulfite solution. The organic phases were subjected to rotary evaporation to remove the solvent, and the residue was subjected to silica gel column chromatography (petroleum ether:ethyl acetate=2:1) to obtain the product (5 g, yield: 41%).

(9) Preparation of tert-butyl 3-(8-amino-7-bromo-6-methyl-2,3-dihydrobenzo[b][1,4]dioxin-5-yl)azetidin-1-carboxylate

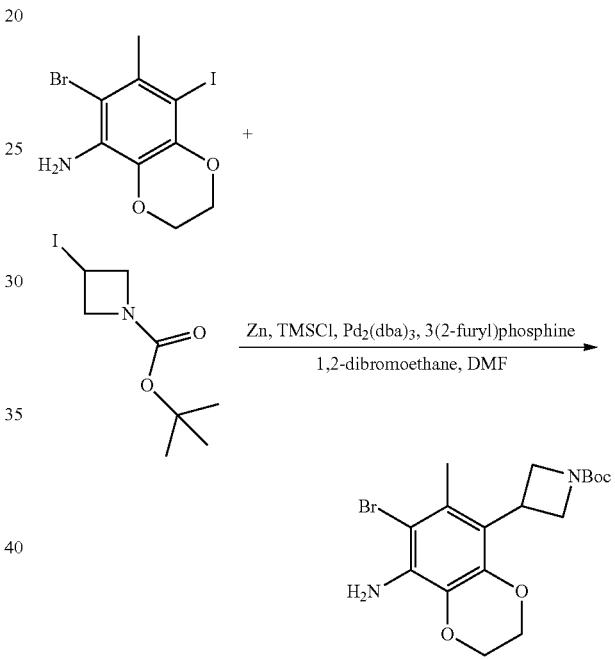

Zinc powder (351.0 mg, 5.40 mmol) was added to 5 mL N,N-dimethyl formamide, and 1,2-dibromoethane (76.1 mg, 0.405 mmol) was added. The resultant mixture was heated to 60° C. and reacted for 10 min. After cooling to room temperature, trimethylchlorosilane (43.7 mg, 0.402 mmol) was added. The resultant mixture was heated to 60° C. and reacted for 10 min. After cooling to room temperature, tert-butyl 3-iodoazetidin-1-carboxylate (1.15 g, 4.06 mmol) was added, and the resultant mixture was stirred at room temperature for 40 min. 6-Bromo-8-iodo-7-methyl-2,3-dihydrobenzo[b][1,4]dioxin-5-amine (1.0 g, 2.70 mmol), tris(dibenzylideneacetone)dipalladium(0) (124 mg, 0.135 mmol) and tri(2-furyl)phosphine (63 mg, 0.271 mmol) were dissolved in 5 mL N,N-dimethyl formamide, and were added to the reaction solution. The resultant mixture was heated to 70° C. and reacted for 16 h. After the reaction, the resultant mixture was filtrated, and the filter cake was washed with 20 mL ethyl acetate. The solvent was removed by rotary evaporation, and the residue was subjected to silica gel column chromatography (petroleum ether:ethyl acetate=2:1) to obtain the product (300 mg, yield: 27.8%).

(10) Preparation of tert-butyl 3-(8-amino-6-methyl-2,3-dihydrobenzo[b][1,4]dioxin-5-yl)azetidin-1-carboxylate

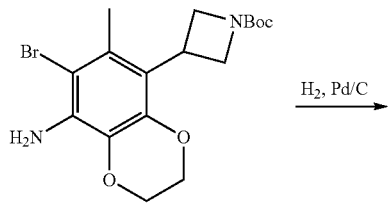

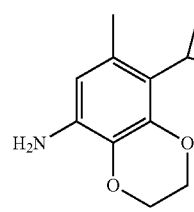

Tert-butyl 3-(8-amino-7-bromo-6-methyl-2,3-dihydrobenzo[b][1,4]dioxin-5-yl)azetidin-1-carboxylate (300 mg, 0.751 mmol) was dissolved in 20 mL methanol, and 250 mg Pd/C was added. With the introduction of hydrogen gas, the reaction was carried out at room temperature overnight. After the reaction, the resultant mixture was filtrated. The solvent was removed by rotary evaporation, and the residue was subjected to silica gel column chromatography (petroleum ether:ethyl acetate=2:1) to obtain the product (120 mg, yield: 50%).

(11) Preparation of 2,5-dichloro-N-(2-(isopropylsulfonyl)phenyl)pyrimidin-4-amine

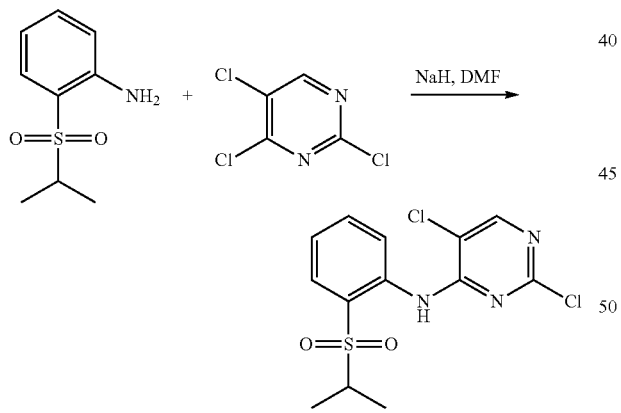

2,4,5-Trichloropyrimidine (4.42 g, 24.1 mmol) was dissolved in 25 mL N,N-dimethyl formamide. In ice water bath, sodium hydride (60%) (1.61 g, 40.2 mmol) was added. After stirring for 10 min, 2-(isopropylsulfonyl)aniline (4.0 g, 20.1 mmol) was slowly added. The resultant mixture was reacted at room temperature for 16 h. After the reaction, 100 mL water was added. The resultant mixture was extracted with ethyl acetate (3×60 mL). The organic phases were combined. The solvent was removed by rotary evaporation, and the residue was subjected to silica gel column chromatography (petroleum ether:ethyl acetate=2:1) to obtain the product (2.0 g, yield: 28.7%).

(12) Preparation of tert-butyl 3-(8-((5-chloro-4-((2-(isopropylsulfonyl)phenyl)amino)pyrimidin-2-yl)amino)-6-methyl-2,3-dihydrobenzo[b][1,4]dioxin-5-yl)azetidin-1-carboxylate

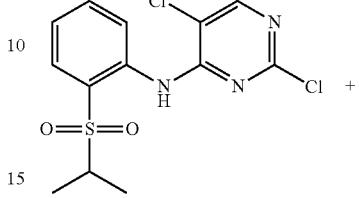

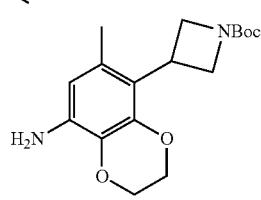

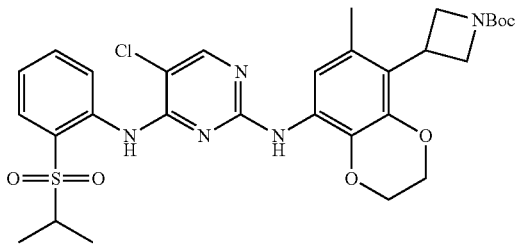

2,5-Dichloro-N-(2-(isopropylsulfonyl)phenyl)pyrimidin-4-amine (156 mg, 0.451 mmol), and tert-butyl 3-(8-amino-6-methyl-2,3-dihydrobenzo[b][1,4]dioxin-5-yl)azetidin-1-carboxylate (120 mg, 0.375 mmol) were dissolved in 10 mL 1,4-dioxane. Tris(dibenzylideneacetone)dipalladium(0) (34 mg, 0.037 mmol), 2-(dicyclohexylphosphino)-2',4',6'-triisopropylbiphenyl (36 mg, 0.0755 mmol) and cesium carbonate (365 mg, 1.12 mmol) were added. The resultant mixture was heated to 80° C. and reacted overnight. After the reaction, the resultant mixture was filtrated. The filtrate was subjected to rotary evaporation to remove the solvent, and the residue was subjected to silica gel column chromatography (petroleum ether:ethyl acetate=2:1) to obtain the product (50 mg, yield: 21%).

(13) Preparation of $N^2$-(8-(azetidin-3-yl)-7-methyl-2,3-dihydrobenzo[b][1,4]dioxin-5-yl)-5-chloro-$N^4$-(2-(isopropylsulfonyl)phenyl)pyrimidine-2,4-diamine

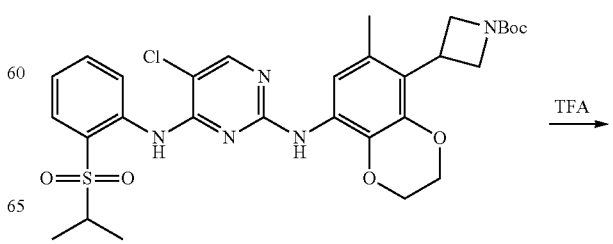

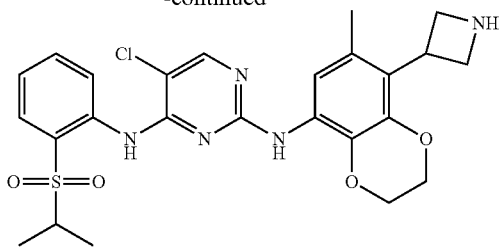

Tert-butyl 3-(8-((5-chloro-4-((2-(isopropylsulfonyl)phenyl)amino)pyrimidin-2-yl)amino)-6-methyl-2,3-dihydrobenzo[b][1,4]dioxin-5-yl)azetidin-1-carboxylate (50 mg, 0.079 mmol) was dissolved in 10 mL dichloromethane, and 2 mL trifluoroacetic acid was added. The resultant mixture was stirred at room temperature for 3 h. After the reaction, the solvent was removed by rotary evaporation, and 50 mL ethyl acetate was added. The resultant mixture was washed with saturated sodium bicarbonate solution, the organic phase was subjected to rotary evaporation to remove the solvent, and the residue was subjected to silica gel column chromatography (dichloromethane:methanol=15:1) to obtain the final product (25 mg, yield: 59.7%).

Molecular formula: $C_{25}H_{28}ClN_5O_4S$ Molecular weight: 530.04 LC-MS (M/e): 530.0[M+H$^+$]

$^1$H-NMR (400 MHz, MeOD) δ: 8.48 (d, J=8.4 Hz, 1H), 8.14 (d, J=6.0 Hz, 1H), 7.90-7.92 (m, 1H), 7.64-7.68 (m, 1H), 7.44 (s, 1H), 7.34-7.37 (m, 1H), 4.52-4.58 (m, 2H), 4.41-4.48 (m, 2H), 4.33-4.39 (m, 5H), 3.44-3.46 (m, 1H), 2.12 (s, 3H), 1.24 (d, J=6.8 Hz, 6H).

Example 7 Preparation of 5-chloro-N$^4$-(2-(isopropylsulfonyl)phenyl)-N$^2$-(6-methyl-5-(1,2,3,6-tetrahydropyridine-4-yl)chroman-8-yl)pyrimidine-2,4-diamine (Compound 8)

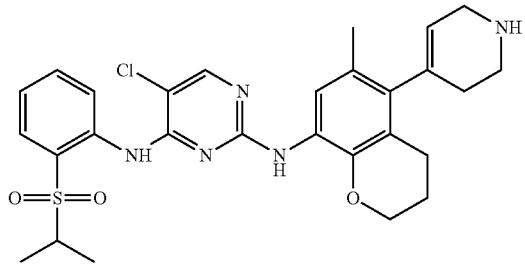 [SMILES: Cc1cc(Nc2ncc(Cl)c(Nc3ccccc3S(=O)(=O)C(C)C)n2)c2c(c1C1=CCNCC1)CCCO2]

(1) Preparation of 1-(allyloxy)-4-methyl-2-nitrobenzene

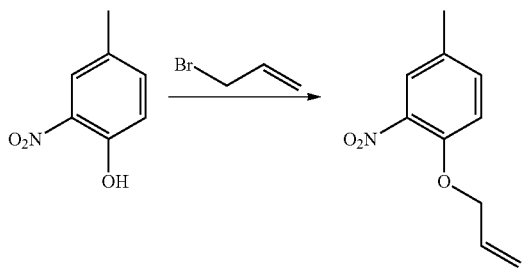

In a 1 L three-necked bottle, under the protection of nitrogen gas, 4-methyl-2-nitrophenol (50 g, 0.327 mol) was added to 500 mL acetone; potassium carbonate (45.1 g, 0.327 mol) was added; and allyl bromide (39.2 g, 0.324 mol) was added in batch. After stirring at room temperature for 24 h, TLC showed that there were still raw materials. 0.5 equivalent potassium carbonate (22.6 g, 0.164 mol) was added. After reacting for 8 h, TLC showed incomplete reaction, and 0.5 equivalent allyl bromide (19.6 g, 0.162 mol) was further added. After reacting at room temperature for 24 h, GC-MS detection showed complete reaction. The system was subjected to rotary evaporation to remove the solvent, and 300 mL water was added. The resultant mixture was extracted with ethyl acetate (100 mL for each time) for three times. The organic phases were combined, washed with saturated NaCl aqueous solution (100 mL), and dried with anhydrous sodium sulphate. The solvent was removed by rotary evaporation to obtain the product (50 g, yield: 79%).

(2) Preparation of 2-allyl-4-methyl-6-nitrophenol

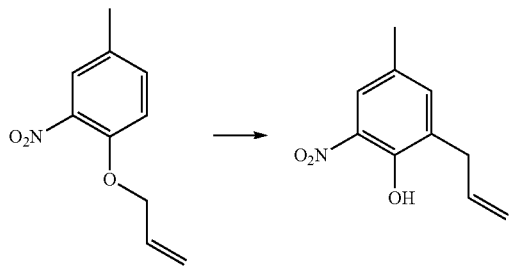

Under the protection of nitrogen gas, in a 100 mL three-necked bottle, 1-(allyloxy)-4-methyl-2-nitrobenzene (23 g, 0.119 mol) was added. After reacting at 190-200° C. for 30 min, GC-MS detection showed complete reaction. The resultant mixture was diluted by adding ethyl acetate (100 mL). After silica gel column chromatography (ethyl acetate:petroleum ether=1:50), the product (11.2 g, yield: 48.7%) was obtained.

(3) Preparation of 2-(3-hydroxypropyl)-4-methyl-6-nitrophenol

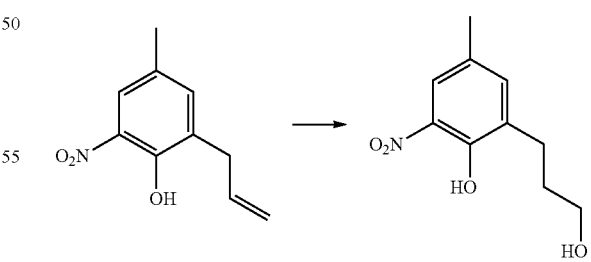

In a 2000 mL three-necked bottle, 2-allyl-4-methyl-6-nitrophenol (22.1 g, 0.115 mol) and tetrahydrofuran (500 mL) were added. Under the protection of nitrogen gas, the mixture was cooled to 0° C. in ice bath. Borane tetrahydrofuran solution (1 mol/L, 240 mL) was added dropwise. After the addition, the ice bath was removed. The resultant mixture was warmed to room temperature naturally and reacted for 4 h. After cooling to 0° C. in ice bath, sodium hydroxide (4.6 g, 0.115 mol) was dissolved in 12 mL water, and added to the system dropwise. After the addition, 30% H₂O₂ (260 mL) was added dropwise. After the addition, the resultant mixture was warmed to room temperature naturally and reacted for 24 h. GC-MS detection showed complete reaction. 300 mL water and 100 mL ethyl acetate were added separately, and the organic phase was separated. The water phase was extracted with ethyl acetate (100 mL×3), washed with saturated NaCl aqueous solution (100 mL), and dried with anhydrous sodium sulphate. The solvent was removed by rotary evaporation. After column chromatography (ethyl acetate:petroleum ether=1:20), the product (16.7 g, yield: 69%) was obtained.

(4) Preparation of 6-methyl-8-nitrochromane

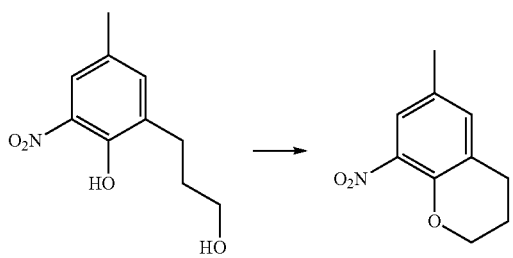

Under the protection of N₂, in a 500 mL three-necked bottle, THF (500 mL) and 2-(3-hydroxypropyl)-4-methyl-6-nitrophenol (16.7 g, 0.079 mol) were added separately. After cooling to 0° C., triphenylphosphine (29.3 g, 0.111 mol) was added in batch. After the addition, DEAD (19.3 g, 0.111 mol) was added dropwise. After the addition, the resultant mixture was warmed to room temperature naturally and reacted for 24 h. GC-MC detection showed complete reaction. 100 mL water was added, and the organic phase was separated. The water phase was extracted with ethyl acetate (50 mL×3). The organic phases were combined, washed with saturated NaCl aqueous solution (100 mL×1), and dried with anhydrous sodium sulphate. The solvent was removed by rotary evaporation. After column chromatography (EA:PE=1:50), the product (8.3 g, yield: 54%) was obtained.

(5) Preparation of 6-methylchroman-8-amine

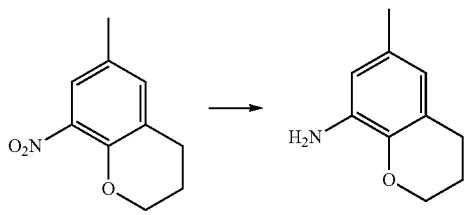

In a 100 mL single-necked bottle, 6-methyl-8-nitrochromane (4 g, 20.7 mmol), ethanol (50 mL), Pd/C (0.5 g, 10%) were added. After replacing air for four times, hydrogen gas was introduced, and the reaction was carried out at room temperature for 3 h. LC-MS detection showed complete reaction. After suction filtration, the filter cake was washed with ethyl acetate (50 mL×3). The filtrate was collected, and was subjected to rotary evaporation to remove the solvent. The residue was directly used in the next step.

(6) Preparation of 5-iodo-6-methylchroman-8-amine

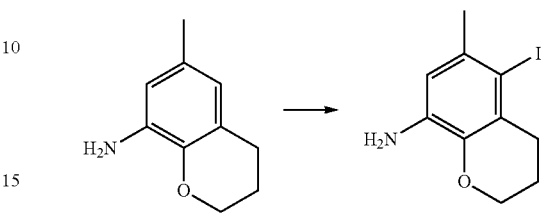

In a 250 mL three-necked bottle, 6-methylchroman-8-amine (500 mg, 3.04 mmol) and HOAc (100 mL) were added. After cooling to 15° C., NIS (0.88 g, 3.96 mmol) was added in batch, and the reaction was carried out at the temperature for 40 min. HOAc was removed by rotary evaporation. The resultant mixture was diluted by adding 300 mLEA, washed with Na₂S₂O₃ solution (100 mL×3), washed with water (100 mL×3), dried with anhydrous Na₂SO₄, filtrated, and concentrated. After column chromatography (PE:EA=100:1-50:1), the product (1.3 g) was obtained.

(7) Preparation of tert-butyl 4-(8-amino-6-methyl-chroman-5-yl)-3,6-dihydropyridine-1(2H)-carboxylate

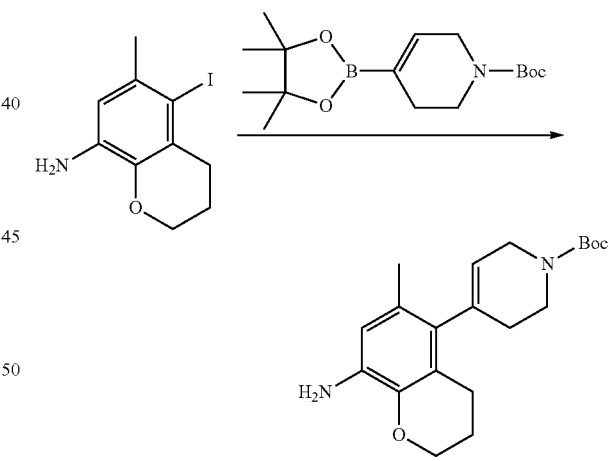

5-Iodo-6-methylchroman-8-amine (289 mg, 1.0 mmol), tert-butyl 4-(4,4,5,5-tetramethyl-1,3,2-dioxaborolan-2-yl)-3,6-dihydropyridine-1 (2H)-carboxylate (310 mg, 1.0 mmol), pd(dppf)Cl₂(29 mg) and cesium carbonate (390 mg, 1.2 mmol) were dissolved in 10 mL 1,4-dioxane. After reacting at 70° C. for 5 h, 50 mL ethyl acetate was added. The resultant mixture was washed with saturated NaCl aqueous solution. The organic phase was dried with anhydrous sodium sulphate, and the solvent was removed by rotary evaporation. After column chromatography (petroleum ether:ethyl acetate=5:1), the product (171 mg, yield: 49.6%) was obtained.

(8) Preparation of 2,5-dichloro-N-(2-(isopropylsulfonyl)phenyl)pyrimidin-4-amine

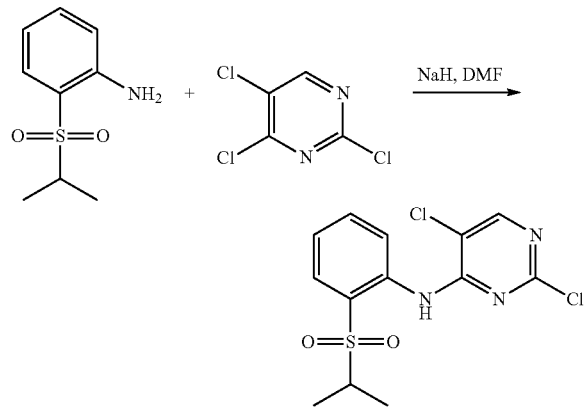

2-(Isopropylsulfonyl)aniline (597 mg, 3.0 mmol) was dissolved in 10 mL THF. In ice water bath, sodium hydride (86.4 mg, 3.6 mmol) was added. After stirring for 10 min, 2,4,5-trichloropyrimidine (549 mg, 3.0 mmol) was added slowly. The resultant mixture was warmed to room temperature and stirred for 2 h. 20 mL saturated NaCl aqueous solution was added. After extraction with dichloromethane, the organic phase was dried with anhydrous sodium sulphate. The solvent was removed by rotary evaporation, and the residue was subjected to silica gel column chromatography (petroleum ether:ethyl acetate=10:1) to obtain the product (306 mg, yield: 29.5%).

(9) Preparation of 5-chloro-$N^4$-(2-(isopropylsulfonyl)phenyl)-$N^2$-(6-methyl-5-(1,2,3,6-tetrahydropyridine-4-yl)chroman-8-yl)pyrimidine-2,4-diamine

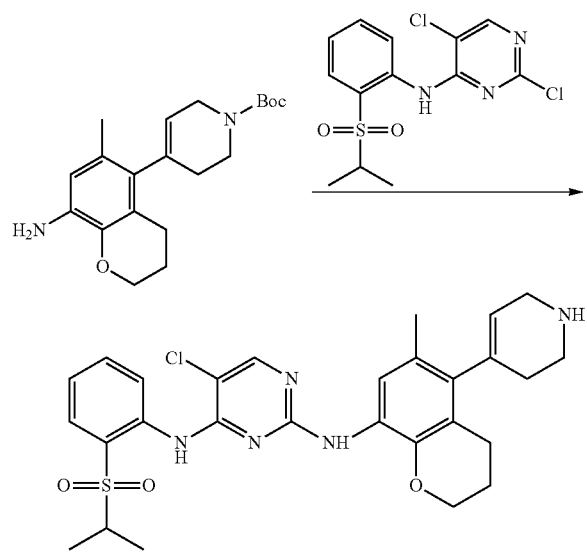

Tert-butyl 4-(8-amino-6-methylchroman-5-yl)-3,6-dihydropyridine-1(2H)-carboxylate (78 mg, 0.23 mmol), 2,5-dichloro-N-(2-(isopropylsulfonyl)phenyl)pyrimidin-4-amine (78 mg, 0.23 mmol), and p-toluene sulfonic acid (39 mg, 0.23 mmol) were dissolved in 5 mL tertiary amyl alcohol. After reacting at 120° C. for 12 h, the resultant mixture was cooled to room temperature, and 20 mL ethyl acetate was added. The resultant mixture was washed with 10 mL saturated sodium bicarbonate solution, and the organic phase was dried with anhydrous sodium sulphate. The solvent was removed by rotary evaporation. After column chromatography (petroleum ether:ethyl acetate=1:1), the final product (70 mg, yield: 56%) was obtained.

Molecular formula: $C_{28}H_{32}ClN_5O_3S$ Molecular weight: 554.11 LC-MS (M/e): 554.0[M+H]$^+$ $^1$H-NMR (400 MHz, MeOD) δ: 8.47 (d, 1H, J=8.0 Hz), 8.09 (s, 1H), 7.88 (dd, 1H, $J_1$=8.0 Hz, $J_2$=1.6 Hz), 7.70 (s, 1H), 7.67 (m, 1H), 7.33 (t, 1H, J=7.2 Hz), 6.07-6.09 (m, 1H), 5.53-5.56 (m, 1H), 4.17 (t, 2H, J=4.8 Hz), 3.79 (d, 2H, J=2.4 Hz), 3.41 (t, 1H, J=6.0 Hz), 3.27-3.29 (m, 2H), 2.73-2.77 (m, 1H), 2.57-2.60 (m, 1H), 2.41 (s, 2H), 2.04 (s, 3H), 1.92-1.98 (m, 2H), 1.25 (d, 6H, J=10.4 Hz).

The above examples are only the exemplified embodiments of the invention, and are not used to limit the protection scope of the invention. The protection scope of the invention is defined by the attached claims.

The present application claims a right of priority on the basis of the previous Chinese patent application No. 201410515596.9 as filed on Sep. 29, 2014, the full text of which is incorporated herein as a part of the present application.

The invention claimed is:

1. A compound of Formula (I), or a pharmaceutically acceptable salt or a stereoisomer thereof:

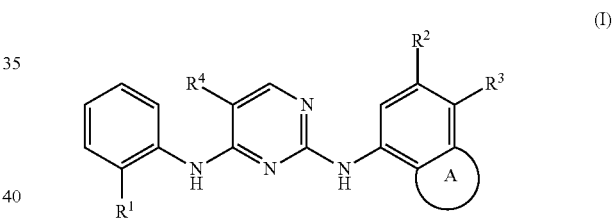

wherein, $R^1$ is selected from the group consisting of —$SO_2R^5$ and —$SO_2NRR^5$;

$R^2$ is selected from the group consisting of hydrogen atom, halogen atom, nitro, cyano, amino, hydroxyl, carboxyl and $C_{1-6}$alkyl;

$R^3$ is selected from the group consisting of 5-6 membered heteroaryl containing 1-2 N atom(s) that is optionally substituted with 1-2 substituent(s) W, and 4-6 membered heterocyclyl containing 1-2 N atom(s) that is optionally substituted with 1-2 substituent(s) W, W is selected from the group consisting of hydroxyl, amino, carboxyl, cyano, nitro, halogen atom, $C_{1-6}$alkyl, $C_{1-6}$alkoxy, $C_{1-6}$alkylamino, ($C_{1-6}$alkyl)$_2$amino, halo-$C_{1-6}$alkyl, halo-$C_{1-6}$alkoxy, $C_{1-6}$alkylcarbonyl, $C_{1-6}$alkylcarbonyloxy and $C_{1-6}$alkylsulfonyl;

$R^4$ is selected from the group consisting of hydrogen atom, halogen atom, cyano, nitro, amino, hydroxyl, carboxyl, $C_{1-6}$alkoxy, $C_{1-6}$alkyl, halo-$C_{1-6}$alkyl, $C_{1-6}$alkylamino, $C_{1-6}$alkylcarbonyl and $C_{1-6}$alkylcarbonyloxy;

R and $R^5$ are independently selected from the group consisting of hydrogen atom and $C_{1-6}$alkyl;

A is selected from the group consisting of 5 membered heterocyclyl containing two O atoms that is optionally substituted with 1-2 substituent(s) Q, and 6 membered heterocyclyl containing two O atoms that is optionally substituted with 1-2 substituent(s) Q; the substituent Q is selected from the group consisting of hydroxyl, amino, carboxyl, cyano, nitro, halogen atom and $C_{1-6}$alkyl.

2. The compound, or the pharmaceutically acceptable salt or stereoisomer thereof according to claim 1,
wherein,
$R^1$ is selected from the group consisting of —$SO_2R^5$ and —$SO_2NRR^5$;
$R^2$ is selected from the group consisting of hydrogen atom, halogen atom, nitro, cyano, amino, hydroxyl, carboxyl and $C_{1-4}$alkyl;
$R^3$ is selected from 4-6 membered heterocyclyl containing 1-2 N atom(s) that is optionally substituted with 1-2 substituent(s) W; W is selected from the group consisting of hydroxyl, amino, carboxyl, cyano, nitro, halogen atom, $C_{1-4}$alkyl, $C_{1-4}$alkoxy, $C_{1-4}$alkylamino, ($C_{1-4}$alkyl)$_2$amino, halo-$C_{1-4}$alkyl, halo-$C_{1-4}$alkoxy, $C_{1-4}$alkylcarbonyl, $C_{1-4}$alkylcarbonyloxy and $C_{1-4}$alkylsulfonyl;
$R^4$ is selected from the group consisting of fluorine atom, bromine atom and chlorine atom;
R and $R^5$ are independently selected from $C_{1-4}$alkyl;
A is selected from the group consisting of 5 membered heterocyclyl containing two O atoms and 6 membered heterocyclyl containing two O atoms, optionally substituted with one substituent Q; the substituent Q is selected from the group consisting of hydroxyl, amino, carboxyl, cyano, nitro, halogen atom and $C_{1-4}$alkyl.

3. The compound, or the pharmaceutically acceptable salt or stereoisomer thereof according to claim 1,
wherein,
$R^1$ is selected from the group consisting of —$SO_2R^5$ and —$SO_2NRR^5$;
$R^2$ is selected from the group consisting of hydrogen atom, halogen atom, nitro, cyano, amino, hydroxyl, carboxyl and $C_{1-4}$alkyl;
$R^3$ is selected from the group consisting of pyridinyl, dihydropyridinyl, tetrahydropyridinyl, azetidinyl, pyrrolyl, dihydropyrrolyl, tetrahydropyrrolyl, pyrazolyl, dihydropyrazolyl, tetrahydropyrazolyl, imidazolyl, dihydroimidazolyl, tetrahydroimidazolyl, pyrimidinyl, dihydropyrimidinyl, tetrahydropyrimidinyl, piperidyl, piperazinyl and morpholinyl;
$R^4$ is selected from the group consisting of fluorine atom, bromine atom and chlorine atom;
R and $R^5$ are independently selected from $C_{1-4}$alkyl;
A is selected from the group consisting of 5 membered heterocyclyl containing two oxygen atoms and 6 membered heterocyclyl containing 2 oxygen atoms, optionally substituted with one substituent Q; the substituent Q is selected from the group consisting of hydroxyl, amino, carboxyl, cyano, nitro, halogen atom and $C_{1-4}$alkyl.

4. The compound, or the pharmaceutically acceptable salt or stereoisomer thereof according to claim 3,
wherein,
$R^1$ is selected from the group consisting of —$SO_2R^5$ and —$SO_2NRR^5$;
$R^2$ is selected from the group consisting of hydrogen atom, halogen atom, nitro, cyano, amino, hydroxyl, carboxyl, methyl, ethyl, propyl, isopropyl, butyl, isobutyl and tert-butyl;
$R^3$ is selected from the group consisting of pyridinyl, dihydropyridinyl, tetrahydropyridinyl, pyrrolyl, dihydropyrrolyl, tetrahydropyrrolyl, azetidinyl, piperidyl, piperazinyl and morpholinyl;
$R^4$ is selected from the group consisting of fluorine atom, bromine atom and chlorine atom;
R and $R^5$ are independently selected from the group consisting of methyl, ethyl, propyl, isopropyl, butyl, isobutyl and tert-butyl;
A is a 6 membered heterocyclyl containing two oxygen atoms, optionally substituted with one substituent Q, the substituent Q is selected from the group consisting of hydroxyl, amino, carboxyl, cyano, nitro, halogen atom, methyl, ethyl, propyl, isopropyl, butyl, isobutyl and tert-butyl.

5. The compound, or the pharmaceutically acceptable salt or stereoisomer thereof according to claim 1, wherein the compound is selected from the group consisting of:

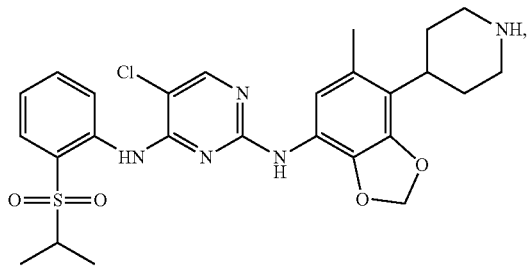

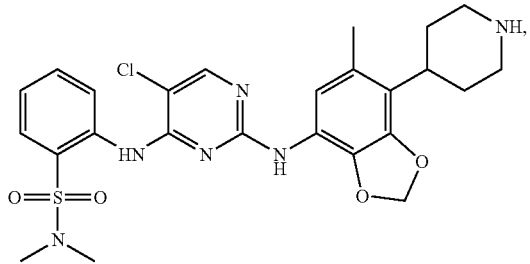

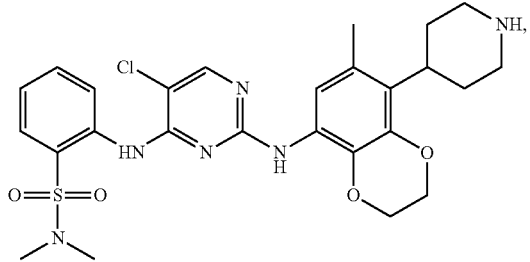

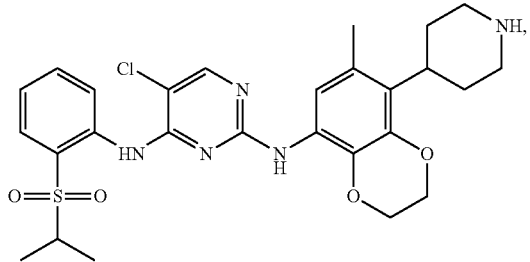

-continued

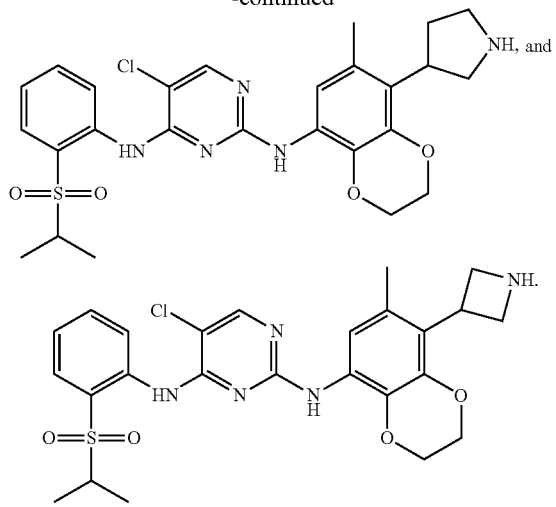

6. A pharmaceutical preparation, prepared from the compound, or the pharmaceutically acceptable salt or stereoisomer thereof according to claim 1, and one or more pharmaceutically acceptable carriers and/or diluents, in any pharmaceutically acceptable dosage form.

7. A pharmaceutical composition comprising the compound, or the pharmaceutically acceptable salt or stereoisomer thereof according to claim 1, further comprising one or more antitumor agents and/or immunosuppressors.

8. The pharmaceutical composition according to claim 7, wherein the antitumor agent and/or immunosuppressor is an antimetabolite, selected from the group consisting of capecitabine, gemcitabine and pemetrexed disodium; or the antitumor agent and/or immunosuppressor is a growth factor inhibitor, selected from the group consisting of pazopanib, imatinib, erlotinib, lapatinib, gefitinib and vandetanib; or the antitumor agent and/or immunosuppressor is an antibody, selected from the group consisting of herceptin and bevacizumab; or the antitumor agent and/or immunosuppressor is amitotic inhibitor, selected from the group consisting of paclitaxel, vinorelbine, docetaxel and doxorubicin; or the antitumor agent and/or immunosuppressor is an antitumor hormone, selected from the group consisting of letrozole, tamoxifen, fulvestrant, flutamide and triptorelin; or the antitumor agent and/or immunosuppressor is an alkylating agent, selected from the group consisting of cyclophosphamide, nitrogen mustard, melphalan, chlorambucil, carmustine and temozolomide; or the antitumor agent and/or immunosuppressor is a metallic platinum, selected from the group consisting of carboplatin, cisplatin and oxaliplatin; or the antitumor agent and/or immunosuppressor is an immunosuppressor, selected from the group consisting of everolimus, sirolimus and temsirolimus; or the antitumor agent and/or immunosuppressor is a purine analog, selected from the group consisting of 6-mercaptopurine, 6-thioguanine and azathioprine; or the antitumor agent and/or immunosuppressor is an antibiotic, selected from the group consisting of Actinomycin D, daunorubicin, doxorubicin, mitoxantrone, bleomycin and plicamycin; or the antitumor agent and/or immunosuppressor is a platinum complex, selected from the group consisting of cisplatin and carboplatin; or the antitumor agent and/or immunosuppressor is an adrenocortical inhibitor, selected from aminoglutethimide; or the antitumor agent and/or immunosuppressor is an enzyme inhibitor, selected from the group consisting of cytarabine, methotrexate, hydroxyurea, hydroxycamptothecin, camptothecin, topotecan andirinotecan.

9. A method for treating an ALK-mediated cancer or non-cancer related disease, comprising administering to a patient in need thereof the compound, or the pharmaceutically acceptable salt or stereoisomer thereof according to claim 1, or a pharmaceutical composition comprising said compound, or the pharmaceutically acceptable salt or stereoisomer thereof, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin or prostate.

10. A method for treating an ALK-mediated cancer or non-cancer related disease, comprising administering to a patient in need thereof the compound, or the pharmaceutically acceptable salt or stereoisomer thereof according to claim 2, or a pharmaceutical composition comprising said compound, or the pharmaceutically acceptable salt or stereoisomer thereof, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin or prostate.

11. A method for treating an ALK-mediated cancer or non-cancer related disease, comprising administering to a patient in need thereof the compound, or the pharmaceutically acceptable salt or stereoisomer thereof according to claim 3, or a pharmaceutical composition comprising said compound, or the pharmaceutically acceptable salt or stereoisomer thereof, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin or prostate.

12. A method for treating an ALK-mediated cancer or non-cancer related disease, comprising administering to a patient in need thereof the compound, or the pharmaceutically acceptable salt or stereoisomer thereof according to claim 4, or a pharmaceutical composition comprising said compound, or the pharmaceutically acceptable salt or stereoisomer thereof, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin or prostate.

13. A method for treating an ALK-mediated cancer or non-cancer related disease, comprising administering to a patient in need thereof the compound, or the pharmaceutically acceptable salt or stereoisomer thereof according to claim 5, or a pharmaceutical composition comprising said compound, or the pharmaceutically acceptable salt or stereoisomer thereof, wherein the cancer related disease is selected from the group consisting of brain carcinoma, lung cancer, squamous cell cancer, bladder carcinoma, gastric cancer, ovarian cancer, peritoneal carcinoma, pancreatic carcinoma, breast cancer, head and neck cancer, cervical cancer, endometrial cancer, colorectal cancer, liver cancer, renal carcinoma, esophageal adenocarcinoma, esophageal squamous cancer, non-Hodgkin lymphoma, central nervous system tumor, prostatic cancer, thyroid cancer, small cell lung cancer, female reproductive duct cancer, cancer in situ, lymphoma, neurofibromatosis, osteocarcinoma, skin cancer, colon cancer, testiculus cancer, non-small cell lung cancer, gastrointestinal stromal tumor, mast cell tumor, multiple myeloma, melanoma, glioma, astrocytoma, neuroblastoma and sarcoma; the non-cancer related disease is selected from benign hyperplasia of skin or prostate.

14. A pharmaceutical preparation, prepared from the compound, or the pharmaceutically acceptable salt or stereoisomer thereof according to claim 5, and one or more pharmaceutically acceptable carriers and/or diluents, in any pharmaceutically acceptable dosage form.

15. A pharmaceutical composition comprising the compound, or the pharmaceutically acceptable salt or stereoisomer thereof according to claim 5, further comprising one or more antitumor agents and/or immunosuppressors.

* * * * *